(12) United States Patent
Zhuang et al.

(10) Patent No.: US 10,073,035 B2
(45) Date of Patent: Sep. 11, 2018

(54) SUB-DIFFRACTION LIMIT IMAGE RESOLUTION AND OTHER IMAGING TECHNIQUES

(71) Applicant: President and Fellows of Harvard College, Cambridge, MA (US)

(72) Inventors: Xiaowei Zhuang, Lexington, MA (US); Wilfred M. Bates, Gottingen (DE); Michael J. Rust, Medford, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 190 days.

(21) Appl. No.: 15/252,307

(22) Filed: Aug. 31, 2016

(65) Prior Publication Data

US 2016/0370295 A1    Dec. 22, 2016

Related U.S. Application Data

(63) Continuation of application No. 14/101,071, filed on Dec. 9, 2013, which is a continuation of application
(Continued)

(51) Int. Cl.
*G01N 21/64* (2006.01)
*C09K 11/06* (2006.01)
(Continued)

(52) U.S. Cl.
CPC .......... *G01N 21/6428* (2013.01); *C09K 11/06* (2013.01); *G01N 15/1429* (2013.01);
(Continued)

(58) Field of Classification Search
CPC ............ C09K 11/06; C09K 2211/1018; C09K 2211/1044; C09K 2211/1475;
(Continued)

(56) References Cited

U.S. PATENT DOCUMENTS 4,549,807 A    10/1985  Harris
6,008,373 A *  12/1999  Waggoner ............ G01N 33/533
                                                         436/6
(Continued)

FOREIGN PATENT DOCUMENTS

CN    1779436 A    5/2006
CN    1963469 A    5/2007
(Continued)

OTHER PUBLICATIONS

Office Action dated Apr. 29, 2009 for U.S. Appl. No. 11/605,842.
(Continued)

*Primary Examiner* — Jennifer Wecker
(74) *Attorney, Agent, or Firm* — Wolf, Greenfield & Sacks, P.C.

(57) ABSTRACT

The present invention generally relates to sub-diffraction limit image resolution and other imaging techniques. In one aspect, the invention is directed to determining and/or imaging light from two or more entities separated by a distance less than the diffraction limit of the incident light. For example, the entities may be separated by a distance of less than about 1000 nm, or less than about 300 nm for visible light. In one set of embodiments, the entities may be selectively activatable, i.e., one entity can be activated to produce light, without activating other entities. A first entity may be activated and determined (e.g., by determining light emitted by the entity), then a second entity may be activated and determined. The entities may be immobilized relative to each other and/or to a common entity. The emitted light may be used to determine the positions of the first and second entities, for example, using Gaussian fitting or other mathematical techniques, and in some cases, with sub-diffraction limit resolution. The methods may thus be used, for example, to determine the locations of two or more entities immobilized relative to a common entity, for example, a
(Continued)

surface, or a biological entity such as DNA, a protein, a cell, a tissue, etc. The entities may also be determined with respect to time, for example, to determine a time-varying reaction. Other aspects of the invention relate to systems for sub-diffraction limit image resolution, computer programs and techniques for sub-diffraction limit image resolution, methods for promoting sub-diffraction limit image resolution, methods for producing photoswitchable entities, and the like.

25 Claims, 22 Drawing Sheets

Related U.S. Application Data

No. 12/795,423, filed on Jun. 7, 2010, which is a continuation of application No. 12/012,524, filed on Feb. 1, 2008, now Pat. No. 7,838,302, which is a continuation-in-part of application No. PCT/US2007/017618, filed on Aug. 7, 2007, which is a continuation of application No. 11/605,842, filed on Nov. 29, 2006, now Pat. No. 7,776,613, said application No. 12/012,524 is a continuation-in-part of application No. 11/605,842, filed on Nov. 29, 2006, now Pat. No. 7,776,613.

(60) Provisional application No. 60/836,170, filed on Aug. 8, 2006, provisional application No. 60/836,167, filed on Aug. 7, 2006.

(51) Int. Cl.
| | | |
|---|---|---|
| *G01N 15/14* | (2006.01) | |
| *G01N 33/58* | (2006.01) | |
| *G02B 21/16* | (2006.01) | |
| *G02B 27/58* | (2006.01) | |
| *G02B 21/00* | (2006.01) | |
| *G02B 21/36* | (2006.01) | |
| *G01N 15/00* | (2006.01) | |

(52) U.S. Cl.
CPC ..... *G01N 15/1475* (2013.01); *G01N 21/6408* (2013.01); *G01N 21/6458* (2013.01); *G01N 33/582* (2013.01); *C09K 2211/1018* (2013.01); *C09K 2211/1044* (2013.01); *C09K 2211/1475* (2013.01); *G01N 2015/0065* (2013.01); *G01N 2021/6421* (2013.01); *G01N 2021/6439* (2013.01); *G01N 2021/6441* (2013.01); *G01N 2201/06113* (2013.01); *G01N 2201/12* (2013.01); *G02B 21/0076* (2013.01); *G02B 21/16* (2013.01); *G02B 21/367* (2013.01); *G02B 27/58* (2013.01)

(58) Field of Classification Search
CPC ........... G01N 15/1429; G01N 15/1475; G01N 2015/0065; G01N 2021/6421; G01N 2021/6439; G01N 2021/6441; G01N 21/6408; G01N 21/6428; G01N 21/6458; G01N 2201/06113; G01N 2201/12; G01N 33/582; G02B 21/16; G02B 21/367; G02B 27/58

See application file for complete search history.

(56) References Cited

U.S. PATENT DOCUMENTS

| | | | |
|---|---|---|---|
| 6,537,829 | B1 | 3/2003 | Zarling et al. |
| 7,430,045 | B2 | 9/2008 | Hell et al. |
| 7,535,012 | B2 | 5/2009 | Betzig et al. |
| 7,626,694 | B2 | 12/2009 | Hess et al. |
| 7,626,695 | B2 | 12/2009 | Hess et al. |
| 7,626,703 | B2 | 12/2009 | Hess et al. |
| 7,710,563 | B2 | 5/2010 | Betzig et al. |
| 7,776,613 | B2 | 8/2010 | Zhuang et al. |
| 7,782,457 | B2 | 8/2010 | Hess et al. |
| 7,803,634 | B2 | 9/2010 | Klimov et al. |
| 7,828,695 | B2 | 11/2010 | Inoue et al. |
| 7,838,302 | B2 | 11/2010 | Zhuang et al. |
| 7,864,314 | B2 | 1/2011 | Betzig et al. |
| 8,110,405 | B2 | 2/2012 | Klimov et al. |
| 8,334,143 | B2 | 12/2012 | Klimov et al. |
| 8,564,792 | B2 | 10/2013 | Zhuang et al. |
| 9,077,975 | B2 | 7/2015 | Zhuang et al. |
| 9,137,516 | B2 | 9/2015 | Zhuang et al. |
| 2002/0064789 | A1 | 5/2002 | Weiss et al. |
| 2003/0087282 | A1 | 5/2003 | Oshida et al. |
| 2006/0038993 | A1 | 2/2006 | Hell |
| 2007/0222974 | A1 | 9/2007 | Zhao et al. |
| 2008/0032414 | A1 | 2/2008 | Zhuang et al. |
| 2008/0068588 | A1 | 3/2008 | Hess et al. |
| 2008/0068589 | A1 | 3/2008 | Hess et al. |
| 2008/0070322 | A1 | 3/2008 | Hess et al. |
| 2008/0070323 | A1 | 3/2008 | Hess et al. |
| 2008/0111086 | A1 | 5/2008 | Betzig et al. |
| 2008/0182336 | A1 | 7/2008 | Zhuang et al. |
| 2009/0206251 | A1 | 8/2009 | Hess et al. |
| 2010/0181497 | A1 | 7/2010 | Hess et al. |
| 2010/0231922 | A1* | 9/2010 | Hess ................... G01B 9/04 356/496 |
| 2010/0283835 | A1 | 11/2010 | Bewersdorf et al. |
| 2010/0297777 | A1 | 11/2010 | Zhuang et al. |
| 2010/0316269 | A1 | 12/2010 | Zhuang et al. |
| 2011/0002530 | A1 | 1/2011 | Zhuang et al. |
| 2012/0009589 | A1 | 1/2012 | Zhuang et al. |
| 2013/0001436 | A1 | 1/2013 | Zhuang et al. |
| 2013/0099136 | A1 | 4/2013 | Klimov et al. |
| 2014/0038201 | A1 | 2/2014 | Zhuang et al. |
| 2014/0063194 | A1 | 3/2014 | Zhuang et al. |
| 2014/0326922 | A1 | 11/2014 | Zhuang et al. |
| 2014/0333750 | A1 | 11/2014 | Zhuang et al. |
| 2016/0202185 | A1 | 7/2016 | Zhuang et al. |

FOREIGN PATENT DOCUMENTS

| | | |
|---|---|---|
| JP | 2002-062261 A | 2/2002 |
| JP | 2004-163277 | 6/2004 |
| JP | 2007-071742 | 3/2007 |
| JP | 2007-140322 A | 6/2007 |
| JP | 2008-542826 | 11/2008 |
| JP | 2010-500563 A | 1/2010 |
| WO | WO 2001/096373 A2 | 12/2001 |
| WO | WO 2004/090617 A2 | 10/2004 |
| WO | WO 2006/123967 A2 | 11/2006 |
| WO | WO 2006/127692 A2 | 11/2006 |
| WO | WO 2008/091296 A2 | 7/2008 |
| WO | WO 2009/085218 A1 | 7/2009 |

OTHER PUBLICATIONS

Office Action dated Nov. 6, 2009 for U.S. Appl. No. 11/605,842.
Office Action dated Jun. 12, 2009 for U.S. Appl. No. 12/012,524.
Office Action dated Jan. 15, 2010 for U.S. Appl. No. 12/012,524.
Office Action dated Apr. 17, 2012 for U.S. Appl. No. 12/795,423.
Office Action dated Oct. 9, 2012 for U.S. Appl. No. 12/795,423.
Final Office Action dated Apr. 4, 2013 for U.S. Appl. No. 12/795,423.
Office Action dated Jul. 16, 2012 for U.S. Appl. No. 12/850,586.
Office Action dated Jan. 30, 2013 for U.S. Appl. No. 12/850,586.
Final Office Action dated Jun. 12, 2013 for U.S. Appl. No. 12/850,586.
Office Action dated Feb. 29, 2012 for U.S. Appl. No. 13/179,936.
Office Action dated Oct. 18, 2012 for U.S. Appl. No. 13/179,936.
Final Office Action dated Apr. 11, 2013 for U.S. Appl. No. 13/179,936.
Office Action dated Feb. 11, 2013 for U.S. Appl. No. 13/551,357.

(56) References Cited

OTHER PUBLICATIONS

Final Office Action dated Jun. 7, 2013 for U.S. Appl. No. 13/551,357.
Office Action dated Oct. 5, 2015 for U.S. Appl. No. 14/101,071.
Office Action dated Apr. 13, 2012 for U.S. Appl. No. 12/746,784.
Office Action dated Sep. 6, 2012 for U.S. Appl. No. 12/746,784.
Office Action dated Jan. 24, 2013 for U.S. Appl. No. 12/746,784.
Office Action dated Apr. 25, 2014 for U.S. Appl. No. 13/899,215.
Final Office Action dated Nov. 26, 2014 for U.S. Appl. No. 13/899,215.
Office Action dated Nov. 25, 2014 for U.S. Appl. No. 14/022,168.
Office Action dated Aug. 16, 2016 for U.S. Appl. No. 14/022,168.
Office Action dated Sep. 15, 2016 for U.S. Appl. No. 14/364,723.
European Office Communication dated Jun. 15, 2009 for Application EP 07872605.6.
European Office Communication dated Sep. 30, 2010 for Application EP 07872605.6.
European Office Communication dated Mar. 14, 2012 for Application EP 07872605.6.
European Office Communication dated Jan. 17, 2014 for Application EP 07872605.6.
Partial European Search Report for EP 11169771.0 dated Mar. 14, 2012.
Extended European Search Report for EP 11169771.0 dated Jul. 6, 2012.
Japanese Office Communication dated Apr. 11, 2012 for JP Application No. 2009-523831.
Japanese Office Action dated Feb. 27, 2013 for JP Application No. 2009-523831.
Japanese Office Action dated Mar. 1, 2013 for JP Application No. 2012-178598.
Japanese Office Action dated Sep. 18, 2013 for JP Application No. 2012-178598.
Japanese Office Action dated Jan. 13, 2015 for Application No. JP 2014-007451.
Japanese Office Action dated Aug. 21, 2015 for Application No. JP 2014-154866.
Japanese Office Action dated Aug. 1, 2016 for Application No. JP 2014-154866.
Japanese Office Action dated Aug. 1, 2016 for Application No. JP 2015-152232.
International Search Report and Written Opinion dated Dec. 15, 2008 for International Patent Application No. PCT/US07/017618.
International Preliminary Report on Patentability dated Feb. 19, 2009 for International Patent Application No. PCT/US07/017618.
Chinese Office Action dated Sep. 27, 2011 for Chinese Application No. 200880121492.2.
Chinese Office Action dated Jun. 6, 2012 for Chinese Application No. 200880121492.2.
Chinese Office Action dated Nov. 19, 2012 for Chinese Application No. 200880121492.2.
Chinese Decision of Rejection dated May 20, 2013 for Application No. 200880121492.2.
Chinese Office Action dated Jan. 15, 2015 for Application No. 200880121492.2.
European Office Action dated Mar. 7, 2016 for Application No. EP 08866669.8.
Japanese Office Action dated Oct. 18, 2012 for JP Application No. 2010-539499.
Japanese Office Action dated Sep. 10, 2013 for JP Application No. 2010-539499.
Japanese Office Action dated Nov. 11, 2014 for Application No. JP 2014-002163.
Japanese Office Action dated Oct. 14, 2015 for Application No. JP 2014-002163.
Japanese Office Action dated Sep. 20, 2016 for Application No. JP 2014-002163.
Japanese Office Action dated Jun. 30, 2015 for Application No. JP 2014-149455.
Japanese Office Action dated May 18, 2016 for Application No. JP 2014-149455.
International Search Report and Written Opinion dated Apr. 23, 2009 for International Patent Application No. PCT/US2008/013915.
International Preliminary Report on Patentability dated Jun. 22, 2010 for International Patent Application No. PCT/US2008/013915.
Invitation to Pay Additional Fees for Application No. PCT/US2012/069138 dated Apr. 2, 2013.
International Search Report and Written Opinion for Application No. PCT/US2012/069138 dated Jul. 2, 2013.
International Preliminary Report on Patentability dated Jun. 26, 2014 for PCT/US2012/069138.
[No Author Listed] Cyan-to-green photoswitchable fluorescent protein PS-CFP2. 2008. <http://www.evrogen.com/protein-descriptions/PS-CFP2-description.pdf> Month not cited on publication.
[No Author Listed] Fluorescence Resonance Energy Transfer (FRET) Microscopy. Olympus Microscopy Resource Center, 2012. Month not cited on publication.
[No Author Listed] Frontiers in live cell imaging/NIGMS and the Cell Migration Consortium (Movie). National Institute of General Medical Sciences, Apr. 20, 2006, http://videocast.nih.gov/launch.asp?13187.
Aitken et al., An oxygen scavenging system for improvement of dye stability in single-molecule fluorescence experiments. Biophys J. Mar. 1, 2008;94(5):1826-35. Epub Oct. 5, 2007.
Amato, Squint-Busters: Tool builders are pushing optical microscope vision to single-molecule sharpness. Chemical and Engineering News. Sep. 4, 2006;49-52.
Ando et al., Regulated fast nucleocytoplasmic shuttling observed by reversible protein highlighting. Science. Nov. 19, 2004;306(5700):1370-3.
Andresen et al., Photoswitchable fluorescent proteins enable monochromatic multilabel imaging and dual color fluorescence nanoscopy. Nat Biotechnol. Sep. 2008;26(9):1035-40.
Antonik et al., Separating structural heterogeneities from stochastic variations in fluorescence resonance energy transfer distributions via photon distribution analysis. J Phys Chem B. Apr. 6, 2006;110(13):6970-8.
Aquino et al., Two-color nanoscopy of three-dimensional volumes by 4Pi detection of stochastically switched fluorophores. Nat Methods. Apr. 2011;8(4):353-9. Epub Mar. 13, 2011.
Bates et al., Multicolor super-resolution imaging with photo-switchable fluorescent probes. Science. Sep. 21, 2007;317(5845):1749-53. Epub Aug. 16, 2007.
Bates et al., Short-range spectroscopic ruler based on a single-molecule optical switch. Phys Rev Lett. Mar. 18, 2005;94(10):108101. Epub Mar. 15, 2005.
Bates et al., Super-resolution microscopy by nanoscale localization of photo-switchable fluorescent probes. Curr Opin Chem Biol. Oct. 2008;12(5):505-14.
Betzig et al., Imaging intracellular fluorescent proteins at nanometer resolution. (Supporting Online Material), http://www.sciencemag.org/cgi/content/full/1127344/DC1, pp. 1-30. Sep. 2006.
Betzig et al., Imaging intracellular fluorescent proteins at nanometer resolution. Science. Sep. 15, 2006;313(5793):1642-5. Epub Aug. 10, 2006.
Betzig, Proposed method for molecular optical imaging. Opt Lett. Feb. 1, 1995;20(3):237-9.
Centonze et al., Fluorescence resonance energy transfer imaging microscopy. Methods Enzymol. 2003;360:542-60. Month not cited on publication.
Dailey et al., Confocal Microscopy of Living Cells. Handbook of Biological Confocal Microscopy. 3rd ed. Jun. 2006, Chapter 19, pp. 381-403.
Dos Remedios et al., Fluorescence resonance energy transfer spectroscopy is a reliable "ruler" for measuring structural changes in proteins. Dispelling the problem of the unknown orientation factor. J Struct Biol. Sep.-Oct. 1995;115(2):175-85.
Eisenstein, New fluorescent protein includes handy on-off switch. Nature Methods. Jan. 2005;2(1):8-9.

(56) References Cited

OTHER PUBLICATIONS

Friedman et al., Viewing dynamic assembly of molecular complexes by multi-wavelength single-molecule fluorescence. Biophys J. Aug. 1, 2006;91(3):1023-31. Epub May 12, 2006.

Gruber et al., Anomalous fluorescence enhancement of Cy3 and cy3.5 versus anomalous fluorescence loss of Cy5 and Cy7 upon covalent linking to IgG and noncovalent binding to avidin. Bioconjug Chem. Sep.-Oct. 2000;11(5):696-704.

Gugel et al., Cooperative 4Pi excitation and detection yields sevenfold sharper optical sections in live-cell microscopy. Biophys J. Dec. 2004;87(6):4146-52. Epub Sep. 17, 2004.

Gustafsson et al., I5M: 3D widefield light microscopy with better than 100 nm axial resolution. J Microsc. Jul. 1999;195(Pt 1):10-6.

Gustafsson et al., Sevenfold improvement of axial resolution in 3D widefield microscopy using two objective lenses. Proceedings of SPIE. 1995;2412:147-56. Month not cited on publication.

Habuchi et al., Reversible single-molecule photoswitching in the GFP-like fluorescent protein Dronpa. Proc Natl Acad Sci U S A. Jul. 5, 2005;102(27):9511-6. Epub Jun. 22, 2005.

Heilemann et al., Carbocyanine dyes as efficient reversible single-molecule optical switch. J Am Chem Soc. Mar. 23, 2005;127(11):3801-6.

Held, An Introduction to Fluorescence Resonance Energy Transfer (FRET) Technology and its Application in Bioscience. BioTek®. Jun. 15, 2005. Available at http://www.biotek.com/resources/docs/Fluorescence_Resonance_Energy_Transfer_Technology_FRET_App_Note.pdf. 8 pages.

Hell et al., Breaking the diffraction resolution limit by stimulated emission: stimulated-emission-depletion fluorescence microscopy. Opt Lett. Jun. 1, 1994;19(11):780-2.

Hell et al., Concepts for nanoscale resolution in fluorescence microscopy. Curr Opin Neurobiol. Oct. 2004;14(5):599-609.

Hell et al., Imaging and writing at the nanoscale with focused visible light through saturable optical transitions. Applied Physics. 2003;77(7):859-60. (The year of publication is sufficiently earlier than the effective U.S. filing date and any foreign priority date so that the particular month of publication is not in issue. See MPEP 609.04(a)).

Hell et al., Properties of a 4Pi confocal fluorescence microscope. J Opt Soc Am A. Dec. 1992;9(12):2159-66.

Hess et al., Ultra-high resolution imaging by fluorescence photoactivation localization microscopy. Biophys J. Dec. 1, 2006;91(11):4258-72. Epub Sep. 15, 2006.

Hofmann et al., Breaking the diffraction barrier in fluorescence microscopy at low light intensities by using reversibly photoswitchable proteins. Proc Natl Acad Sci U S A. Dec. 6, 2005;102(49):17565-9. Epub Nov. 28, 2005.

Hohng et al., Single-Molecule Three-Color FRET. Biophysical J. Aug. 2004. 87: 1328-37.

Huang et al., Three-dimensional super-resolution imaging by stochastic optical reconstruction microscopy. Science. Feb. 8, 2008;319(5864):810-3. Epub Jan. 3, 2008.

Huang et al., Whole-cell 3D STORM reveals interactions between cellular structures with nanometer-scale resolution. Nat Methods. Dec. 2008;5(12):1047-52. Epub Nov. 23, 2008.

Jones et al., Fast, three-dimensional super-resolution imaging of live cells. Nat Methods. Jun. 2011;8(6):499-505. Epub May 8, 2011.

Juette et al., Three-dimensional sub-100 nm resolution fluorescence microscopy of thick samples. Nat Methods. Jun. 2008;5(6):527-9. Epub May 11, 2008.

Kao et al., Tracking of single fluorescent particles in three dimensions: Use of cylindrical optics to encode particle position. Biophys J. Sep. 1994;67(3):1291-300.

Kenworthy et al., Imaging protein-protein interactions using fluorescence resonance energy transfer microscopy. Methods. Jul. 2001;24(3):289-96.

LaCoste et al., Ultrahigh-resolution multicolor colocalization of single fluorescent probes. Proc Natl Acad Sci U S A. Aug. 15, 2000;97(17):9461-6.

Linde et al., Photoswitching microscopy with subdiffraction-resolution. Proc SPIE. Feb. 24, 2009;7185:71850F1-11.

Osterman et al., White Paper: Near-infrared fluorescence imaging: Seeing beyond the visible with IRDye infrared dyes. 2012. Available at http://biosupport.licor.com/docs/IRDyes--HOPaper_v8.pdf. Last accessed Feb. 25, 2013. 18 pages. Month not cited on publication.

Pavani et al., Three-dimensional, single-molecule fluorescence imaging beyond the diffraction limit by using a double-helix point spread function. Proc Natl Acad Sci U S A. Mar. 3, 2009;106(9):2995-9. Epub Feb 11, 2009.

Prabhat et al., Simultaneous imaging of several focal planes in fluorescence microscopy for the study of cellular dynamics in 3D. Proc of SPIE. Feb. 2006;6090:60900L-1-60900L-7.

Ram et al., Improved single particle localization accuracy with dual objective multifocal plane microscopy. Opt Express. Apr. 13, 2009;17(8):6881-98.

Rust et al., Sub-diffraction-limit imaging by stochastic optical reconstruction microscopy (STORM). Nat Methods. Oct. 2006;3(10):793-5. Epub Aug. 9, 2006.

Sahoo et al., A 10-A spectroscopic ruler applied to short polyprolines.J Am Chem Soc. Aug. 8, 2007;129(31):9762-72. Epub Jul. 13, 2007.

Schmidt et al., Mitochondrial cristae revealed with focused light. Nano Lett. Jun. 2009;9(6):2508-10.

Schmidt et al., Spherical nanosized focal spot unravels the interior of cells. Nat Methods. Jun. 2008;5(6):539-44. Epub May 18, 2008.

Shtengel et al., Interferometric fluorescent super-resolution microscopy resolves 3D cellular ultrastructure. Proc Natl Acad Sci U S A. Mar. 3, 2009;106(9):3125-30. Epub Feb. 6, 2009.

Souslova et al., Photoswitchable cyan fluorescent protein as a FRET donor. Microsc Res Tech. Mar. 2006;69(3):207-9.

Speidel et al., Three-dimensional tracking of fluorescent nanoparticles with subnanometer precision by use of off-focus imaging. Opt Lett. Jan. 15, 2003;28(2):69-71.

Toprak et al., Three-dimensional particle tracking via bifocal imaging. Nano Lett. Jul. 2007;7(7):2043-5. Epub Jun. 21, 2007.

Truong et al., The use of FRET imaging microscopy to detect protein-protein interactions and protein conformational changes in vivo. Curr Opin Struct Biol. Oct. 2001;11(5):573-8.

Van De Linde et al., Multicolor photoswitching microscopy for subdiffraction-resolution fluorescence imaging. Photochem Photobiol Sci. Apr. 2009;8(4):465-9. Epub Feb. 9, 2009.

Van Oijen et al., 3-Dimensional super-resolution by spectrally selective imaging. Chemical Physics Letters. Jul. 1998;292:183-187.

Vaziri et al., Multilayer three-dimensional super resolution imaging of thick biological samples. Proc Natl Acad Sci U S A. Dec. 23, 2008;105(51):20221-6. Epub Dec. 16, 2008.

Wang et al., Label-free detection of small-molecule-protein interactions by using nanowire nanosensors. Proc Natl Acad Sci U S A. Mar. 1, 2005;102(9):3208-12. Epub Feb. 16, 2005.

Widengren et al., Characterization of Photoinduced Isomerization and Back-Isomerization of the Cyanine Dye Cy5 by Fluorescence Correlation Spectroscopy. J Phys Chem A. 2000;104(27):6416-6428. Published on web Jun. 17, 2000.

Xu et al., Dual-objective STORM reveals three-dimensional filament organization in the actin cytoskeleton. Nat Methods. Jan. 8, 2012;9(2):185-8. doi: 10.1038/nmeth.1841.

Xu et al., Dual-objective Storm reveals three-dimensional filament organization in the actin cytoskeleton. Nat Methods. Jan. 8, 2012;9(2):185-8. doi: 10.1038/nmeth.1841. Supplementary Information.

Yildiz et al., Fluorescence imaging with one nanometer accuracy: Application to molecular motors. Acc Chem Res. 2005;38(7):574-82. Published online Mar. 23, 2005.

Zhuang, Nano-imaging with STORM. Nat Photonics. Jul. 2009;3(7):365-367.

\* cited by examiner

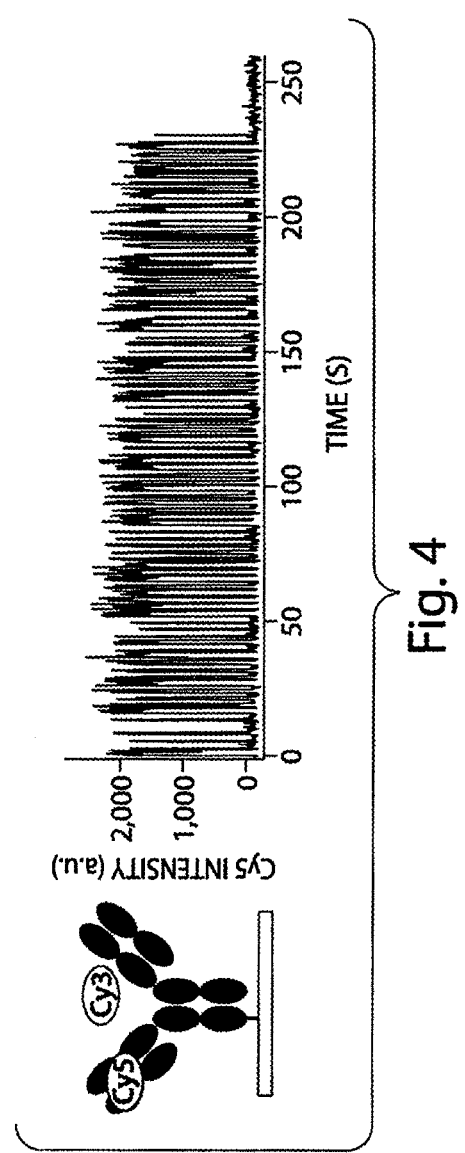

CLATHRIN COATED PITS
MICROTUBULES

Fig. 13A
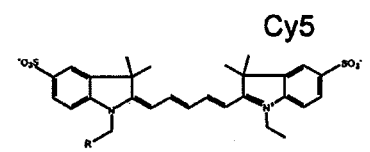
Fig. 13B
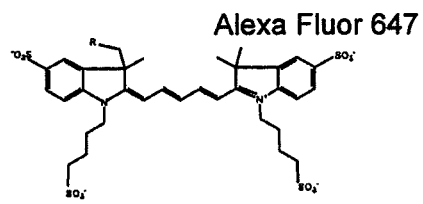
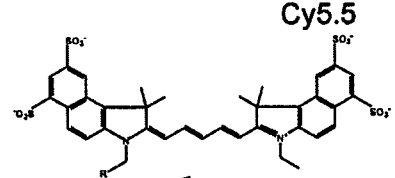
FIG. 13C
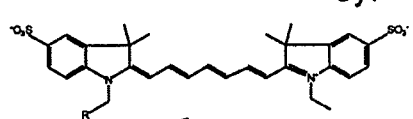
FIG. 13D
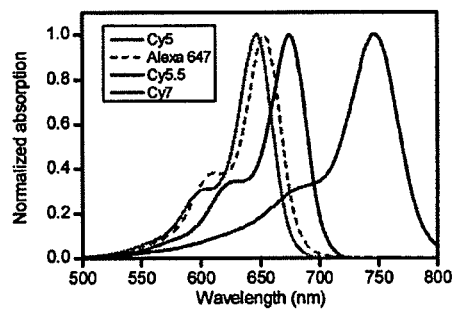
FIG. 13E
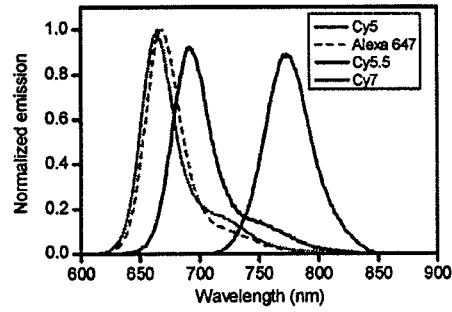
FIG. 13F
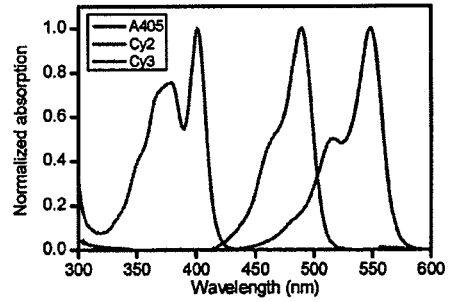
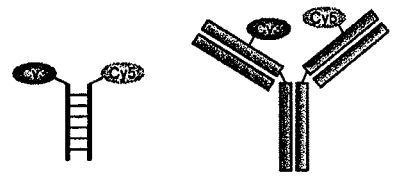
Fig. 13G
Fig. 13H Fig. 19A
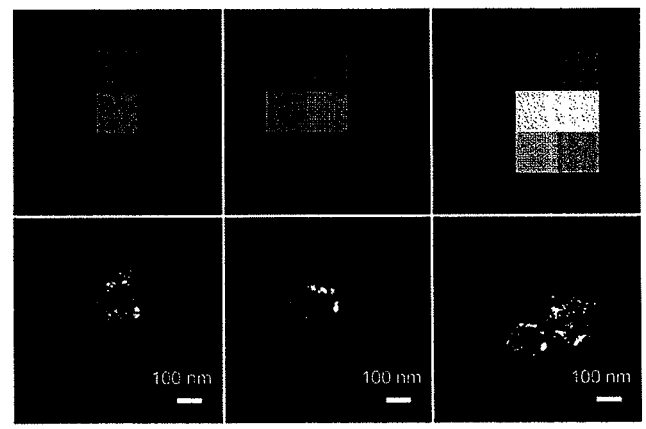
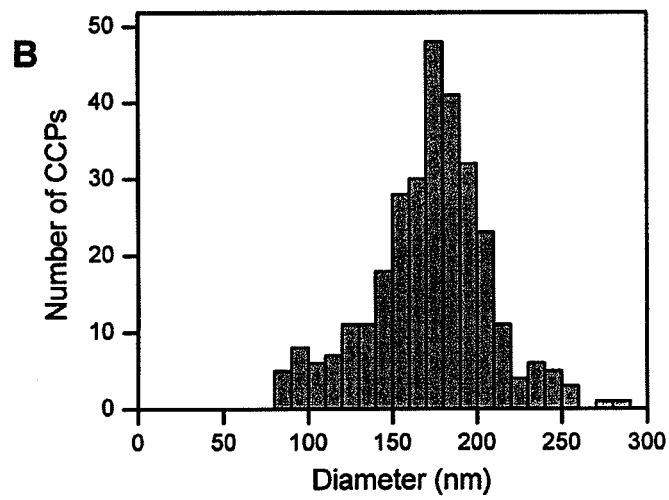
Fig. 19B

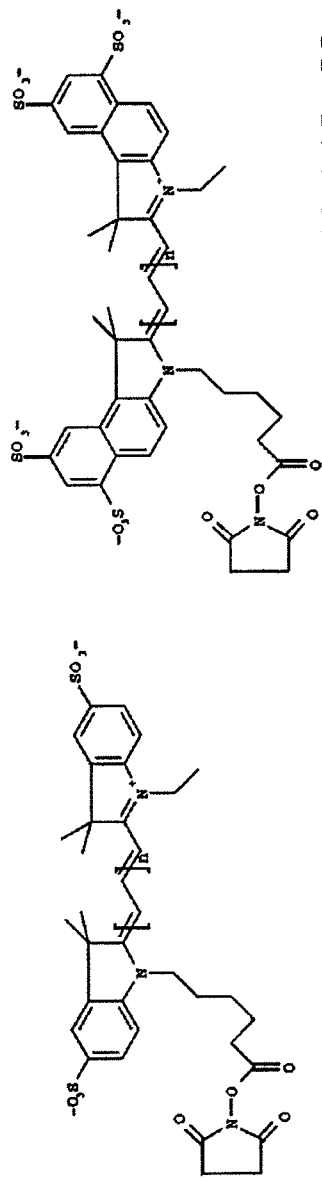
Fig. 20A
Fig. 20B
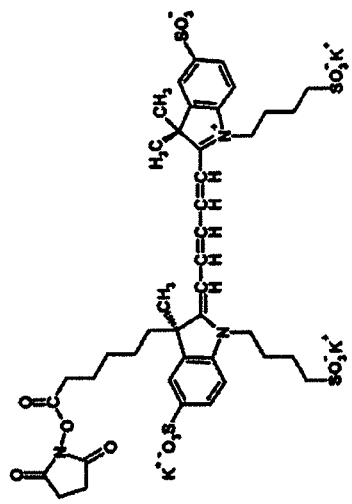
Fig. 20C

SUB-DIFFRACTION LIMIT IMAGE RESOLUTION AND OTHER IMAGING TECHNIQUES

RELATED APPLICATIONS

This application claims priority to all of the following according to the following recitation of priority relationships. This application is a continuation of U.S. patent application Ser. No. 14/101,071, filed Dec. 9, 2013, entitled "Sub-Diffraction Limit Image Resolution and Other Imaging Techniques," which is a continuation of U.S. patent application Ser. No. 12/795,423, filed Jun. 7, 2010, entitled "Sub-Diffraction Limit Image Resolution and Other Imaging Techniques," which is a continuation of U.S. patent application Ser. No. 12/012,524, filed Feb. 1, 2008, entitled "Sub-Diffraction Limit Image Resolution and Other Imaging Techniques," which is a continuation-in-part of International Patent Application No. PCT/US2007/017618, filed Aug. 7, 2007, entitled "Sub-Diffraction Limit Image Resolution and Other Imaging Techniques," which is a continuation-in-part of U.S. patent application Ser. No. 11/605,842, filed Nov. 29, 2006, entitled "Sub-Diffraction Image Resolution and Other Imaging Techniques," which claims the benefit of U.S. Provisional Patent Application Ser. No. 60/836,167, filed Aug. 7, 2006, entitled "Sub-Diffraction Image Resolution," and the benefit of U.S. Provisional Patent Application Ser. No. 60/836,170, filed Aug. 8, 2006, entitled "Sub-Diffraction Image Resolution." Said Ser. No. 12/012,524 is also a continuation-in-part of said Ser. No. 11/605,842, which claims the benefit of said Ser. Nos. 60/836,167 and 60/836,170. Each of the above is incorporated herein by reference.

GOVERNMENT FUNDING

This invention was made with U.S. Government support under GM068518 awarded by the National Institutes of Health and under N66001-04-1-8903 awarded by U.S. Navy SPAWAR/SD. The U.S. Government has certain rights in the invention.

FIELD OF INVENTION

The present invention generally relates to sub-diffraction limit image resolution and other imaging techniques.

BACKGROUND

Fluorescence microscopy is widely used in molecular and cell biology and other applications for non-invasive, time-resolved imaging. Despite these advantages, standard fluorescence microscopy is not useful for ultra-structural imaging, due to a resolution limit set by the diffraction of light. Several approaches have been employed to try to pass this diffraction limit, including near-field scanning optical microscopy (NSOM), multi-photon fluorescence, stimulated emission depletion (STED), reversible saturable optical linear fluorescence transition (RESOLFT), and saturated structured-illumination microscopy (SSIM), but each has certain unsatisfactory limitations. Electron microscopy is often used for high resolution imaging of biological samples, but microscopy uses electrons, rather than light, and is difficult to use with biological samples due to its preparation requirements. Accordingly, new techniques are needed to harness the benefits of fluorescence microscopy for ultra-resolution imaging of biological and other samples.

SUMMARY OF THE INVENTION

The present invention generally relates to sub-diffraction limit image resolution and other imaging techniques. The subject matter of the present invention involves, in some cases, interrelated products, alternative solutions to a particular problem, and/or a plurality of different uses of one or more systems and/or articles.

The invention is a method, in one aspect. In one set of embodiments, the method includes acts of providing a first entity and a second entity separated by a distance of less than about 1000 nm, determining light emitted by the first entity, determining light emitted by the second entity, and determining the positions of the first entity and the second entity by using the light emitted by the first entity and the light emitted by the second entity. In another set of embodiments, the method includes acts of providing a first entity and a second entity separated by a distance of less than about 1000 nm, activating the first entity but not the second entity, determining light emitted by the first entity, activating the second entity, determining light emitted by the second entity, and determining the positions of the first entity and the second entity by using the light emitted by the first entity and the light emitted by the second entity.

The method, according to yet another set of embodiments, includes acts of providing a plurality of entities able to emit light, at least some of which are separated by a distance of less than about 1000 nm, activating a fraction of the plurality of entities to emit light, determining the emitted light, deactivating the activated fraction of the plurality of entities, and repeating the acts of activating and deactivating the plurality of entities to determine the positions of the plurality of entities.

In another set of embodiments, the method includes acts of providing a first entity and a second entity separated by a distance of separation, determining light emitted by the first entity, the light emitted by the first entity having a wavelength greater than the distance of separation, determining light emitted by the second entity, and determining the positions of the first entity and the second entity by using the light emitted by the first entity and the light emitted by the second entity. The method, in yet another set of embodiments, includes acts of providing a first entity and a second entity separated by a distance of separation, activating the first entity but not the second entity, determining light emitted by the first entity, the light emitted by the first entity having a wavelength greater than the distance of separation, activating the second entity, determining light emitted by the second entity, and determining the positions of the first entity and the second entity by using the light emitted by the first entity and the light emitted by the second entity.

In one set of embodiments, the method includes acts of providing a plurality of entities able to emit light, at least some of which are separated by a distance of separation less than the wavelength of the emitted light, activating a fraction of the plurality of entities to emit light, determining the emitted light, deactivating the activated fraction of the plurality of entities, and repeating the acts of activating and deactivating the plurality of entities to determine the positions of the plurality of entities.

The method, in another set of embodiments, includes acts of providing a first entity and a second entity separated by a distance of less than about 1000 nm where the first entity and the second entity each are immobilized relative to a common entity, determining the positions of the first entity and the second entity at a first point of time, determining the positions of the first entity and the second entity at a second point of time, and determining movement and/or structural changes of the common entity using the positions of the first and second entities at the first and second points of time. In some cases, the entities may be resolved or imaged in time. One or both of these entities may be photoactivatable or photoswitchable in some cases. The two entities may be chemically identical or distinct, for example, to allow multi-color imaging. In yet another set of embodiments, the method includes acts of providing a first entity and a second entity separated by a distance of separation where the first entity and the second entity are each immobilized relative to a common entity, determining the positions of the first entity and the second entity at a first point of time using light emitted by the first entity and light emitted by the second entity where the light emitted by the first entity has a wavelength greater than the distance of separation, determining the positions of the first entity and the second entity at a second point of time, and determining movement and/or structural changes of the common entity using the positions of the first and second entities at the first and second points of time. In some cases, the entities may be resolved or imaged in time. One or both of these entities may be photoactivatable or photoswitchable in some cases. The two entities may be chemically identical or distinct, for example, to allow multi-color imaging.

In still another set of embodiments, the method includes acts of identifying, within a series of images in time, one or more light-emission regions, each generated by a single entity; for each light-emission region, identifying the center of the light-emission region; and for each light-emission region, reconstructing the position of the single entity generating the light-emission region at a resolution greater than the wavelength of the light emitted by the single entity. Some or all of these entities may be photoactivatable or photoswitchable. The entities may be chemically identical or distinct for example, to allow multi-color imaging.

In another aspect, the invention is directed to an article including a translation stage for a microscope having a drift of less than about 100 nm/min, and/or an article including time-modulated light sources that can be switched on and off periodically and/or in a programmed fashion, and/or an article including detectors for detecting fluorescence emission.

Still another aspect of the invention is directed to an imaging composition. The composition, according to one set of embodiments, includes a light-emitting entity, capable of being reversibly or irreversibly switched between a first state able to emit light at a first, emission wavelength and a second state that does not substantially emit light at the first wavelength. In one embodiment, the light-emitting entity comprises a first portion that is capable of emitting light at the first wavelength, and a second portion that activates the first portion upon exposure to an external stimulus, thereby causing the first portion to emit light at the first wavelength.

In another aspect, the present invention is directed to a system for performing one or more of the embodiments described herein. In another aspect, the present invention is directed to computer programs and techniques for performing one or more of the embodiments described herein. For example, one embodiment of the invention is directed to a machine-readable medium comprising a program, embodied in the medium, for causing a machine to perform a method comprising acts of identifying, within a series of images in time, one or more light-emission regions, each generated by a single entity; for each light-emission region, identifying the center of the light-emission region; and for each light-emission region, reconstructing the position of the single entity generating the light-emission region at a resolution greater than the wavelength of the light emitted by the single entity.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4 illustrates the repeated switching of Cy3-Cy5-labeled antibody, in accordance with one embodiment of the invention;

FIGS. 13A-13H illustrate various chemical structures and properties of certain entities of the invention;

FIGS. 19A-B shows images of various clathrin-coated pits, in yet another embodiment of the invention; and FIGS. 20A-20F show various emissive entities containing succinimide moieties.

DETAILED DESCRIPTION

Figure 1A:
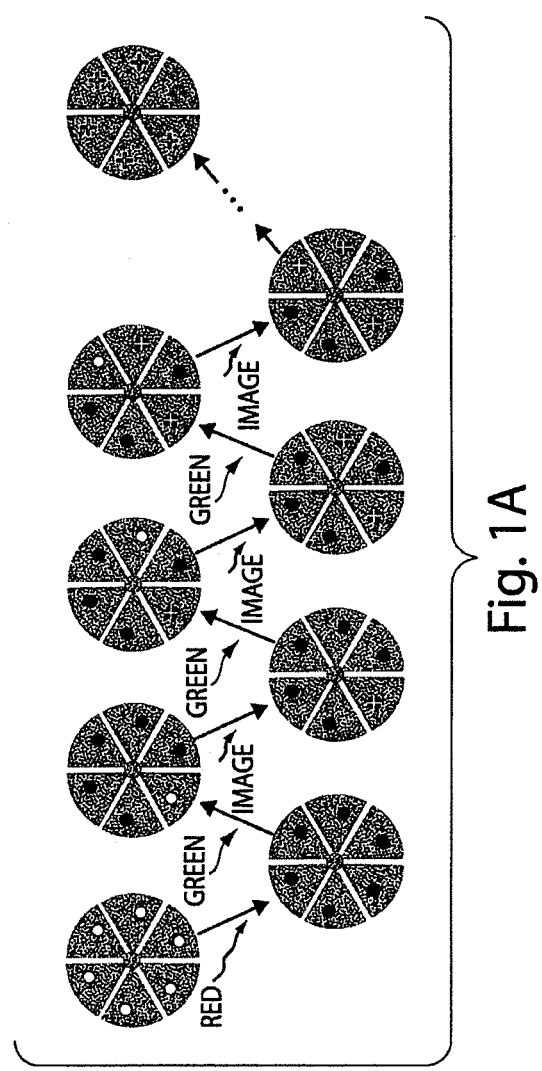
FIGS. 1A-1B illustrate the principle of sub-diffraction limit resolution imaging, according to one embodiment of the invention, and a photoswitchable Cy3-Cy5 moiety.

The present invention generally relates to sub-diffraction limit image resolution and other imaging techniques. In one aspect, the invention is directed to determining and/or imaging light from two or more entities separated by a distance less than the diffraction limit of the incident light. For example, the entities may be separated by a distance of less than about 1000 nm, or less than about 300 nm for visible light. In one set of embodiments, the entities may be selectively activatable, i.e., one entity can be activated to produce light, without activating other entities. A first entity may be activated and determined (e.g., by determining light emitted by the entity), then a second entity may be activated and determined. The entities may be immobilized relative to each other and/or to a common entity. The emitted light may be used to determine the positions of the first and second entities, for example, using Gaussian fitting or other mathematical techniques, and in some cases, with sub-diffraction limit resolution. The methods may thus be used, for example, to determine the locations of two or more entities immobilized relative to (directly or indirectly, e.g., via a linker) a common entity, for example, a surface, or a biological entity such as DNA, a protein, a cell, a tissue, a biomolecular complex, etc. The entities may also be determined with respect to time, for example, to determine a time-varying reaction. Other aspects of the invention relate to systems for sub-diffraction limit image resolution, computer programs and techniques for sub-diffraction limit image resolution, methods for promoting sub-diffraction limit image resolution, methods for producing photoswitchable entities, and the like.

In various aspects of the invention, any entity able to emit light may be used. The entity may be a single molecule in some cases. Non-limiting examples of emissive entities include fluorescent entities (fluorophores) or phosphorescent entities, for example, cyanine dyes (e.g., Cy2, Cy3, Cy5, Cy5.5, Cy7, etc.) metal nanoparticles, semiconductor nanoparticles or "quantum dots," or fluorescent proteins such as GFP (Green Fluorescent Protein). Other light-emissive entities are readily known to those of ordinary skill in the art. As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 700 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical or at least substantially chemically identical.

In one set of embodiments, the entity is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state. An entity is "photoactivatable" if it can be activated by incident light of a suitable wavelength. As a non-limiting example, Cy5, can be switched between a fluorescent and a dark state in a controlled and reversible manner by light of different wavelengths, i.e., 633 nm red light can switch or deactivate Cy5 to a stable dark state, while 532 nm green light can switch or activate the Cy5 back to the fluorescent state. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light, i.e., the entity is "photoswitchable." Thus, the photoswitchable entity can be switched between different light-emitting or non-emitting states by incident light, e.g., of different wavelengths. The light may be monochromatic (e.g., produced using a laser) or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a much reduced intensity) when exposed to the excitation wavelength.

In one set of embodiments, as discussed, a switchable entity may be switched upon exposure to light. In some cases, the light used to activate the switchable entity may come from an external source (e.g., a light source such as a fluorescent light source, another light-emitting entity proximate the switchable entity, etc.). The second, light emitting entity, in some cases, may be a fluorescent entity, and in certain embodiments, the second, light-emitting entity may itself also be a switchable entity. In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa Fluor 405 (Invitrogen), Alexa Fluor 488 (Invitrogen), Cy2 (GE Healthcare), Cy3 (GE Healthcare), Cy3B (GE Healthcare), Cy3.5 (GE Healthcare), or other suitable dyes. Examples of light-emitting portions include, but are not limited to, Cy5, Cy5.5 (GE Healthcare), Cy7 (GE Healthcare), Alexa Fluor 647 (Invitrogen), Alexa Fluor 680 (Invitrogen), Alexa Fluor 700 (Invitrogen), Alexa Fluor 750 (Invitrogen), Alexa Fluor 790 (Invitrogen), DiD, DiR, YOYO-3 (Invitrogen), YO-PRO-3 (Invitrogen), TOT-3 (Invitrogen), TO-PRO-3 (Invitrogen) or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, Alexa Fluor 647-Alexa Fluor 405, Alexa Fluor 647-Alexa Fluor 488, Alexa Fluor 647-Cy2, Alexa Fluor 647-Cy3, or Alexa Fluor 647-Cy3.5. The structures of Cy3, Cy5, Cy5.5, and Cy7 are shown in FIG. 7, with a non-limiting example of a linked version of Cy3-Cy5 shown in FIG. 7E; those of ordinary skill in the art will be aware of the structures of these and other compounds, many of which are available commercially. The portions may be linked via a covalent bond, or by a linker, such as those described in detail below. Other light-emitting or activator portions may include portions having two quaternized nitrogen atoms joined by a polymethine chain, where each nitrogen is independently part of a heteroaromatic moiety, such as pyrrole, imidazole, thiazole, pyridine, quinoine, indole, benzothiazole, etc., or part of a nonaromatic amine. In some cases, there may be 5, 6, 7, 8, 9, or more carbon atoms between the two nitrogen atoms.

In certain cases, the light-emitting portion and the activator portions, when isolated from each other, may each be fluorophores, i.e., entities that can emit light of a certain, emission wavelength when exposed to a stimulus, for example, an excitation wavelength. However, when a switchable entity is formed that comprises the first fluorophore and the second fluorophore, the first fluorophore forms a first, light-emitting portion and the second fluorophore forms an activator portion that switches that activates or "switches" the first portion in response to a stimulus. For example, the switchable entity may comprise a first fluorophore directly bonded to the second fluorophore, or the first and second entity may be connected via a linker or a common entity. Whether a pair of light-emitting portion and activator portion produces a suitable switchable entity can be tested by methods known to those of ordinary skills in the art. For example, light of various wavelength can be used to stimulate the pair and emission light from the light-emitting portion can be measured to determined wither the pair makes a suitable switch.

As a non-limiting example, Cy3 and Cy5 may be linked together to form such an entity. Such a procedure is described in more detail in the Examples, below. In this example, Cy3 is an activator portion that is able to activate Cy5, the light-emission portion. Thus, light at or near the absorption maximum (e.g., near 532 nm light for Cy3) of the activation or second portion of the entity may cause that portion to activate the first, light-emitting portion, thereby causing the first portion to emit light (e.g., near 633 nm for Cy5). As previously described, the first, light-emitting portion can subsequently be deactivated by any suitable technique (e.g., by directing 633 nm red light to the Cy5 portion of the molecule).

Other non-limiting examples of potentially suitable activator portions include 1,5 IAEDANS, 1,8-ANS, 4-Methylumbelliferone, 5-carboxy-2,7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-Hydroxy Tryptamine (HAT), 5-ROX (carboxy-X-rhodamine), 5-TAMRA (5-Carboxytetramethylrhodamine), 6-Carboxyrhodamine 6G, 6-CR 6G, 6-JOE, 7-Amino-4-methylcoumarin, 7-Aminoactinomycin D (7-AAD), 7-Hydroxy-4-methylcoumarin, 9-Amino-6-chloro-2-methoxyacridine, ABQ, Acid Fuchsin, ACMA (9-Amino-6-chloro-2-methoxyacridine), Acridine Orange, Acridine Red, Acridine Yellow, Acriflavin, Acriflavin Feulgen SITSA, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alizarin Complexon, Alizarin Red, AMC, AMCA-S, AMCA (Aminomethylcoumarin), AMCA-X, Aminoactinomycin D, Aminocoumarin, Aminomethylcoumarin (AMCA), Anilin Blue, Anthrocyl stearate, APTRA-BTC, APTS, Astrazon Brilliant Red 4G, Astrazon Orange R, Astrazon Red 6B, Astrazon Yellow 7 GLL, Atabrine, ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 647, ATTO 647N, ATTO 655, ATTO 680, ATTO 700, ATTO 725, ATTO 740, ATTO-TAG CBQCA, ATTO-TAG FQ, Auramine, Aurophosphine G, Aurophosphine, BAO 9 (Bisaminophenyloxadiazole), BCECF (high pH), BCECF (low pH), Berberine Sulphate, Bimane, Bisbenzamide, Bisbenzimide (Hoechst), bis-BTC, Blancophor FFG, Blancophor SV, BOBO-1, BOBO-3, Bodipy 492/515, Bodipy 493/503, Bodipy 500/510, Bodipy 505/515, Bodipy 530/550, Bodipy 542/563, Bodipy 558/568, Bodipy 564/570, Bodipy 576/589, Bodipy 581/591, Bodipy 630/650-X, Bodipy 650/665-X, Bodipy 665/676, Bodipy Fl, Bodipy FL ATP, Bodipy Fl-Ceramide, Bodipy R6G, Bodipy TMR, Bodipy TMR-X conjugate, Bodipy TMR-X, SE, Bodipy TR, Bodipy TR ATP, Bodipy TR-X SE, BO-PRO-1, BO-PRO-3, Brilliant Sulphoflavin FF, BTC, BTC-5N, Calcein, Calcein Blue, Calcium Crimson, Calcium Green, Calcium Green-1 $Ca^{2+}$ Dye, Calcium Green-2 $Ca^{2+}$, Calcium Green-5N $Ca^{2+}$, Calcium Green-C18 $Ca^{2+}$, Calcium Orange, Calcofluor White, Carboxy-X-rhodamine (5-ROX), Cascade Blue, Cascade Yellow, Catecholamine, CCF2 (GeneBlazer), CFDA, Chromomycin A, Chromomycin A, CL-NERF, CMFDA, Coumarin Phalloidin, CPM Methylcoumarin, CTC, CTC Formazan, Cy2, Cy3.1 8, Cy3.5, Cy3, Cy5.1 8, cyclic AMP Fluorosensor (FiCRhR), Dabcyl, Dansyl, Dansyl Amine, Dansyl Cadaverine, Dansyl Chloride, Dansyl DHPE, Dansyl fluoride, DAPI, Dapoxyl, Dapoxyl 2, Dapoxyl 3' DCFDA, DCFH (Dichlorodihydrofluorescein Diacetate), DDAO, DHR (Dihydorhodamine 123), Di-4-ANEPPS, Di-8-ANEPPS (non-ratio), DiA (4-Di-16-ASP), Dichlorodihydrofluorescein Diacetate (DCFH), DiD-Lipophilic Tracer, DiD (DiIC18(5)), DIDS, Dihydrohodamine 123 (DHR), DiI (DiIC18(3)), Dinitrophenol, DiO (DiOC18(3)), DiR, DiR (DiIC18(7)), DM-NERF (high pH), DNP, Dopamine, DTAF, DY-630-NHS, DY-635-NHS, DyLight 405, DyLight 488, DyLight 549, DyLight 633, DyLight 649, DyLight 680, DyLight 800, ELF 97, Eosin, Erythrosin, Erythrosin ITC, Ethidium Bromide, Ethidium homodimer-1 (EthD-1), Euchrysin, EukoLight, Europium (III) chloride, Fast Blue, FDA, Feulgen (Pararosaniline), FIF (Formaldehyd Induced Fluorescence), FITC, Flazo Orange, Fluo-3, Fluo-4, Fluorescein (FITC), Fluorescein Diacetate, Fluoro-Emerald, Fluoro-Gold (Hydroxystilbamidine), Fluor-Ruby, FluorX, FM 1-43, FM 4-46, Fura Red (high pH), Fura Red/Fluo-3, Fura-2, Fura-2/BCECF, Genacryl Brilliant Red B, Genacryl Brilliant Yellow 10GF, Genacryl Pink 3G, Genacryl Yellow 5GF, GeneBlazer (CCF2), Gloxalic Acid, Granular blue, Haematoporphyrin, Hoechst 33258, Hoechst 33342, Hoechst 34580, HPTS, Hydroxycoumarin, Hydroxystilbamidine (FluoroGold), Hydroxytryptamine, Indo-1, high calcium, Indo-1, low calcium, Indodicarbocyanine (DiD), Indotricarbocyanine (DiR), Intrawhite Cf, JC-1, JO-JO-1, JO-PRO-1, LaserPro, Laurodan, LDS 751 (DNA), LDS 751 (RNA), Leucophor PAF, Leucophor SF, Leucophor WS, Lissamine Rhodamine, Lissamine Rhodamine B, Calcein/Ethidium homodimer, LOLO-1, LO-PRO-1, Lucifer Yellow, Lyso Tracker Blue, Lyso Tracker Blue-White, Lyso Tracker Green, Lyso Tracker Red, Lyso Tracker Yellow, LysoSensor Blue, LysoSensor Green, LysoSensor Yellow/Blue, Mag Green, Magdala Red (Phloxin B), Mag-Fura Red, Mag-Fura-2, Mag-Fura-5, Mag-Indo-1, Magnesium Green, Magnesium Orange, Malachite Green, Marina Blue, Maxilon Brilliant Flavin 10 GFF, Maxilon Brilliant Flavin 8 GFF, Merocyanin, Methoxycoumarin, Mitotracker Green FM, Mitotracker Orange, Mitotracker Red, Mitramycin, Monobromobimane, Monobromobimane (mBBr-GSH), Monochlorobimane, MPS (Methyl Green Pyronine Stilbene), NBD, NBD Amine, Nile Red, Nitrobenzoxadidole, Noradrenaline, Nuclear Fast Red, Nuclear Yellow, Nylosan Brilliant lavin E8G, Oregon Green, Oregon Green 488-X, Oregon Green, Oregon Green 488, Oregon Green 500, Oregon Green 514, Pacific Blue, Pararosaniline (Feulgen), PBFI, Phloxin B (Magdala Red), Phorwite AR, Phorwite BKL, Phorwite Rev, Phorwite RPA, Phosphine 3R, PKH26 (Sigma), PKH67, PMIA, Pontochrome Blue Black, POPO-1, POPO-3, PO-PRO-1, PO-PRO-3, Primuline, Procion Yellow, Propidium Iodid (PI), PyMPO, Pyrene, Pyronine, Pyronine B, Pyrozal Brilliant Flavin 7GF, QSY 7, Quinacrine Mustard, Resorufin, RH 414, Rhod-2, Rhodamine, Rhodamine 110, Rhodamine 123, Rhodamine 5 GLD, Rhodamine 6G, Rhodamine B, Rhodamine B 200, Rhodamine B extra, Rhodamine BB, Rhodamine BG, Rhodamine Green, Rhodamine Phallicidine, Rhodamine Phalloidine, Rhodamine Red, Rhodamine WT, Rose Bengal, S65A, S65C, S65L, S65T, SBFI, Serotonin, Sevron Brilliant Red 2B, Sevron Brilliant Red 4G, Sevron Brilliant Red B, Sevron Orange, Sevron Yellow L, SITS, SITS (Primuline), SITS (Stilbene Isothiosulphonic Acid), SNAFL calcein, SNAFL-1, SNAFL-2, SNARF calcein, SNARF1, Sodium Green, SpectrumAqua, SpectrumGreen, SpectrumOrange, Spectrum Red, SPQ (6-methoxy-N-(3-sulfopropyl)quinolinium), Stilbene, Sulphorhodamine B can C, Sulphorhodamine Extra, SYTO 11, SYTO 12, SYTO 13, SYTO 14, SYTO 15, SYTO 16, SYTO 17, SYTO 18, SYTO 20, SYTO 21, SYTO 22, SYTO 23, SYTO 24, SYTO 25, SYTO 40, SYTO 41, SYTO 42, SYTO 43, SYTO 44, SYTO 45, SYTO 59, SYTO 60, SYTO 61, SYTO 62, SYTO 63, SYTO 64, SYTO 80, SYTO 81, SYTO 82, SYTO 83, SYTO 84, SYTO 85, SYTOX Blue, SYTOX Green, SYTOX Orange, Tetracycline, Tetramethylrhodamine (TAMRA), Texas Red, Texas Red-X conjugate, Thiadicarbocyanine (DiSC3), Thiazine Red R, Thiazole Orange, Thioflavin 5, Thioflavin S, Thioflavin TCN, Thiolyte, Thiozole Orange, Tinopol CBS (Calcofluor White), TMR, TO-PRO-1, TO-PRO-3, TO-PRO-5, TOTO-1, TOTO-3, TRITC (tetramethylrodamine isothiocyanate), True Blue, TruRed, Ultralite, Uranine B, Uvitex SFC, WW 781, X-Rhodamine, XRITC, Xylene Orange, Y66F, Y66H, Y66W, YO-PRO-1, YO-PRO-3, YOYO-1, YOYO-3, SYBR Green, Thiazole orange (interchelating dyes), or combinations thereof.

Accordingly, in one embodiment of the invention, a light-emitting switchable entity is provided, comprising a first, light emitting portion and a second, activation portion. The entity has a maximum emission wavelength determined by the first, light emitting portion and a maximum activation wavelength determined by the second, activation portion. Notably, the two wavelengths are not controlled by the same molecular entity, and are effectively decoupled. In some cases, the same wavelength light can be used both for activating the emitting portion to a fluorescent state and for exciting emission from and deactivating the emitting portion. Further, multiple types of switchable entities within a sample may be independently determined. For example, two switchable entities having the same activator portions but different light-emission portions can be activated by the same wavelength light applied to the sample, but emit at different wavelengths due to different light-emission portions and can be easily distinguished, even at separation distances of less than sub-diffraction limit resolutions. This can effectively yield two colors in the image. Similarly, two switchable entities having the same light-emission portions but different activator portions can be activated by different wavelength light applied to the sample, due to the different activator portions, and the light-emission portions may emit at same wavelengths and can thus be distinguished, even at separation distances of less than sub-diffraction limit resolutions. This also can effectively yield two colors in the image. When these methods are combined, four (or more) color images can be readily produced. Using this principle, multi-color imaging can be scaled up to 6 colors, 9 colors, etc., depending on the switchable and/or activator entities. This multi-color imaging principle may also be used with the imaging methods described herein to yield sub-diffraction limit resolutions, and/or used to obtained multi-color images with other imaging methods not limited to sub-diffraction limit resolutions.

In contrast, fluorescent dyes commonly used by those of ordinary skill in the art (e.g., isolated Cy5) inherently have a maximum excitation wavelength and a maximum emission wavelength that are each determined by the nature and structure of the fluorescent dye, and cannot be independently controlled. Thus, the invention, in another set of embodiments, provides a range of switchable entities where the first, light emitting portion and the second, activation portion are each independently selected. Accordingly, in some embodiments, a larger set of colors is provided, e.g., with respect to conventional imaging methods.

Any suitable method may be used to link the first, light-emitting portion and the second, activation portion. For instance, the light-emitting and the activation portions may be covalently bonded to each other, for example, using the techniques described below. In some cases, a linker is used, and is chosen such that the distance between the first and second portions is sufficiently close to allow the activator portion to activate the light-emitting portion as desired, e.g., whenever the light-emitting portion has been deactivated in some fashion. Typically, the portions will be separated by distances on the order of 500 nm or less, for example, less than about 300 nm, less than about 100 nm, less than about 50 nm, less than about 20 nm, less than about 10 nm, less than about 5 nm, less than about 2 nm, less than about 1 nm, etc. Examples of linkers include, but are not limited to, carbon chains (e.g., alkanes or alkenes), optionally including one or more heteroatoms, polymer units, a biological molecule such as a nucleic acid (DNA, RNA, PNA, LNA, or the like), a lipid molecule, a protein or a polypeptide, a carbohydrate or polysaccharide molecule, or the like.

In some cases, a linker comprising a rigid portion may be used. As used herein, a "rigid" portion means a portion of a molecule, the ends of which are separated by a distance which cannot change (outside of normal molecule-scale changes in temperature, etc.) without breaking at least one bond. Examples of rigid portions include aryl or alkyne groups. For example, the linker may include phenyl, pyridinyl, biphenyl, xylyl, acetylene, or the like. The light-emitting portion and/or the activator portion may be attached to the linker using any suitable technique. In some embodiments, the technique may include the use of attachment systems including an electrophile-nucleophile combination. For example, the light-emitting portion and/or the activator portion may comprise an electrophilic atom, which refers to an atom which may be attacked by, and forms a new bond to, a nucleophilic atom (e.g., an atom having a reactive pair of electrons). In some cases, the electrophilic atom may comprise a suitable leaving group. The electrophilic atom can be attached to (e.g., reacted with) a linker comprising a nucleophilic atom. In some embodiments, the technique includes reacting a light-emitting portion and/or the activator portion comprising a nucleophilic atom with a linker comprising an electrophilic atom. Non-limiting examples of functional groups comprising electrophilic atoms include a carbonyl group such as an aldehyde, an ester, a carboxylic acid, a ketone, an amide (e.g., iodoacetamide), an anhydride, an acid chloride, a hydrazone, a succinimide, a maleimide group, or an alpha, beta-unsaturated ketone. Examples of functional groups comprising nucleophilic atoms include, but are not limited to, a thiol, a hydroxyl group, an amine, a hydrazide, or the like.

Non-limiting examples of potentially useful attachment systems include succinimide-amine (e.g., producing an amide), maleimide-thiol or iodoacetamide-thiol (e.g., producing a thiol ester or a thiol ether), amine-carboxylic acid, hydrazide-aldehyde or hydrazide-ketone (e.g., producing an amine or an imine), disulfide bonds, or the like. As an example, a light-emitting portion may contain a succinimide moiety (positioned anywhere in the light-emitting portion), and be reacted with a nucleic acid linker (e.g., DNA) containing one or more amine groups, a protein linker (e.g., an antibody or an enzyme) containing one or more amine groups, etc. Similarly, an activator portion may be attached to the linker using the same, or different techniques. For instance, the activator portion may contain a maleimide moiety, which can react with a thiol on the protein linker. In some cases, such moieties can be commercially obtained. As a specific, non-limiting example, certain dyes such as Cy3 and Cy5 are commercially sold conjugated to succinimide moieties, and certain nucleic acids are sold modified to include various amine groups at certain locations, such that the dyes can be conjugated to the nucleic acids via succinimide-amine reactions. As another example, an amine-modified Alexa 647, which may be obtained commercially, can be directly bonded to a bis-functional Cy3 NHS (N-hydroxysuccinimide) ester (also obtainable commercially) via a succidimide-amine attachment method.

Thus, in some cases, a succinimide moiety and/or a maleimide moiety may be attached to the light-emitting portion and/or the activator portion, and the succinimide moiety and/or maleimide moiety may be covalently bonded to amines such as primary amines, e.g., on a linker. Non-limiting examples of light-emitting or activators containing such moieties are shown in FIGS. 20A-20F. The light-emitting portion and/or the activator portion may be bonded to a linker, or to each other, using such moieties. Examples of compounds having such moieties include those discussed above; structural formulae of some of these compounds can be seen in the figures. As used herein, a "succinimide moiety" is a moiety having a general succinimide structure, e.g.:

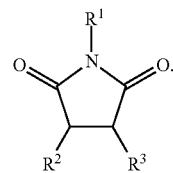

Similarly, a "maleimide moiety" is a moiety having a general maleimide structure, e.g.:

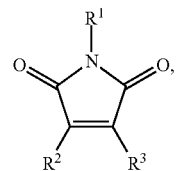

where each of $R^1$, $R^2$, and $R^3$ in the above structures independently is a hydrogen atom (i.e., succinimide or maleimide, respectively) or represents other, non-hydrogen atoms or group of atoms, for example, halogens, alkyls, alkoxyls, etc. In some cases, at least one of $R^1$, $R^2$, and $R^3$ may indicate attachment of the succinimide or maleimide moiety to a linker.

Those of ordinary skill in the art would be able to select other attachment systems suitable for use in the context of the invention. For example, the light-emitting portion and/or the activator portion may be attached to the linker via pericyclic reactions (e.g., Diels-Alder reactions, cycloadditions, etc.), Wittig reactions, metal-catalyzed reactions (e.g., cross-coupling reactions), and the like.

In some cases, the light-emitting portion and/or the activator portion may contain more than one functional group, one or more of which may be used to attach the portion to the linker. For example, the light-emitting portion and/or the activator portion may comprise two functional groups (e.g., a bi-functional portion), which may be the same or different. Those of ordinary skill in the art would be able to synthesize compositions of the invention utilizing such bi-functional, tri-functional, or other multi-functional portions. For example, the synthesis may comprise the use of one or more protecting groups to alter the reactivity of one functional group relative to another functional group, such that the functional groups may be reacted in a particular manner at a selected point in the synthesis. In an illustrative embodiment, a light-emitting portion may comprise two amine groups, where one amine may be reacted with di-tert-butyl dicarbonate to form a "protected" amine (e.g., N-tert-butoxycarbonyl- or t-BOC-protected) having reduced reactivity relative to the un-protected amine, under a particular set of conditions. The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. Other protecting groups are described in, for example, Greene, T. W., Wuts, P. G. M. *Protective Groups in Organic Synthesis, 2nd* ed., Wiley: New York, 1991.

In one set of embodiments of the invention, the light-emitting switchable entity can also include other switchable fluorescent probes that do not necessarily include the two portions, such as, but not limited to, photoactivatable or photoswitchable dye molecules, natural or engineered fluorescent proteins that are photoactivatable or photoswitchable, photoactivatable or photoswitchable inorganic particles, or the like. In some cases, the switchable entity may include a first, light-emitting portion and a second, activation portion, as discussed herein.

In one set of embodiments, the switchable entity can be immobilized, e.g., covalently, with respect to a binding partner, i.e., a molecule that can undergo binding with a particular analyte. Binding partners include specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. Other examples include, but are not limited to, an enzyme would specifically bind to its substrate, a nucleic acid would specifically bind to its complement, an antibody would specifically bind to its antigen. The binding may be by one or more of a variety of mechanisms including, but not limited to ionic interactions, and/or covalent interactions, and/or hydrophobic interactions, and/or van der Waals interactions, etc. By immobilizing a switchable entity with respect to the binding partner of a target molecule or structure (e.g., DNA or a protein within a cell), the switchable entity can be used for various determination or imaging purposes. For example, a switchable entity having an amine-reactive group may be reacted with a binding partner comprising amines, for example, antibodies, proteins or enzymes. A non-limiting example of the immobilization of a switchable entity to an antibody is discussed in the Examples, below.

In some embodiments, more than one switchable entity may be used, and the entities may be the same or different. In some cases, the light emitted by a first entity and the light emitted by a second entity have the same wavelength. The entities may be activated at different times and the light from each entity may be determined separately. This allows the location of the two entities to be determined separately and, in some cases, the two entities may be spatially resolved, as discussed in detail below, even at distances of separation that are less than the light emitted by the entities or below the diffraction limit of the emitted light (i.e., "sub-diffraction limit" resolutions). In certain instances, the light emitted by a first entity and the light emitted by a second entity have different wavelengths (for example, if the first entity and the second entity are chemically different, and/or are located in different environments). The entities may be spatially resolved even at distances of separation that are less than the light emitted by the entities or below the diffraction limit of the emitted light. In certain instances, the light emitted by a first entity and the light emitted by a second entity have substantially the same wavelengths, but the two entities may be activated by light of different wavelengths and the light from each entity may be determined separately. The entities may be spatially resolved even at distances of separation that are less than the light emitted by the entities, or below the diffraction limit of the emitted light.

In some embodiments, the first, light-emitting portion and the second, activation portion as described above may not be directly covalently bonded or linked via a linker, but are each immobilized relative to a common entity. In other embodiments, two or more of the switchable entities (some of which can include, in certain cases, a first, light-emitting portion and a second, activation portion linked together directly or through a linker) may be immobilized relative to a common entity in some aspects of the invention. The common entity in any of these embodiments may be any nonbiological entity or biological entity, for example, a cell, a tissue, a substrate, a surface, a polymer, a biological molecule such as a nucleic acid (DNA, RNA, PNA, LNA, or the like), a lipid molecule, a protein or a polypeptide, or the like, a biomolecular complex, or a biological structure, for example, an organelle, a microtubule, a clathrin-coated pit, etc. The common entity may accordingly be determined in some fashion, e.g., imaged. As another example, two or more entities may be immobilized relative to a DNA strand or other nucleic acid strand (e.g., using antibodies, substantially complementary oligonucleotides labeled with one or more entities, chemical reactions or other techniques known to those of ordinary skill in the art), and their locations along the strand detected. In some cases, the number of base pairs (bp) separating the entities along the nucleic acid strand may be determined.

In some cases, the entities may be independently switchable, i.e., the first entity may be activated to emit light without activating a second entity. For example, if the entities are different, the methods of activating each of the first and second entities may be different (e.g., the entities may each be activated using incident light of different wavelengths). As another non-limiting example, incident light having a sufficiently weak intensity may be applied to the first and second entities such that only a subset or fraction of the entities within the incident light are activated, i.e., on a stochastic or random basis. Specific intensities for activation can be determined by those of ordinary skill in the art using no more than routine skill By appropriately choosing the intensity of the incident light, the first entity may be activated without activating the second entity.

The second entity may be activated to emit light, and optionally, the first entity may be deactivated prior to activating the second entity. The second entity may be activated by any suitable technique, as previously described, for instance, by application of suitable incident light.

In some cases, incident light having a sufficiently weak intensity may be applied to a plurality of entities such that only a subset or fraction of the entities within the incident light are activated, e.g., on a stochastic or random basis. The amount of activation may be any suitable fraction, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the entities may be activated, depending on the application. For example, by appropriately choosing the intensity of the incident light, a sparse subset of the entities may be activated such that at least some of them are optically resolvable from each other and their positions can be determined. Iterative activation cycles may allow the positions of all of the entities, or a substantial fraction of the entities, to be determined. In some cases, an image with sub-diffraction limit resolution can be constructed using this information.

The two or more entities may be resolved, even at distances of separation that are less than the wavelength of the light emitted by the entities or below the diffraction limit of the emitted light, according to another aspect of the invention. The resolution of the entities may be, for instance, on the order of 1 micrometer (1000 nm) or less, as described herein. For example, if the emitted light is visible light, the resolution may be less than about 700 nm. In some cases, two (or more) entities may be resolved even if separated by a distance of less than about 500 nm, less than about 300 nm, less than about 200 nm, less than about 100 nm, less than about 80 nm, less than about 60 nm, less than about 50 nm, or less than about 40 nm. In some cases, two or more entities separated by a distance of at least about 20 nm or less than 10 nm can be resolved using embodiments of the present invention.

Light emitted by each of the switchable entities may be determined, e.g., as an image or matrix. For example, the first entity may be activated and the light emitted by the first entity determined, and the second entity may be activated (with or without deactivating the first entity) and light emitted by the second entity may be determined. The light emitted by each of the plurality of entities may be at the same or different wavelengths. Any suitable method may be used to determine the emitted light. For instance, a camera such as a CCD camera, a photodiode, a photomultiplier, or a spectrometer may be used; those of ordinary skill in the art will know of other suitable techniques. Additional non-limiting example of a suitable technique for determining light produced by the entities is discussed in the Examples, below. In some cases, multiple images (or other determinations) may be used, for example, to improve resolution and/or to reduce noise. For example, at least 2, at least 5, at least 10, at least 20, at least 25, at least 50, at least 75, at least 100, etc. images may be determined, depending on the application.

In some aspects, the light may be processed to determine the spatial positions of the two or more entities. In some cases, the positions of one or more entities, distributed within an image, may each be individually determined. In one set of embodiments, the emitted light may be processed, using Gaussian fitting or other suitable techniques, to localize the position of each of the emissive entities. Details of one suitable Gaussian fit technique are described in the Examples, below; those of ordinary skill in the art will be able to identify other suitable image-processing techniques with the benefit of the present disclosure.

Another example of an image-processing technique follows, in accordance with another embodiment of the invention. Starting with a series of images of a sample (e.g., a movie), each light-emission peak (e.g., through fluorescence, phosphorescence, etc.) is identified, and the times which the peak is present are determined. For example, a peak may be present with approximately the same intensity in a series of images with respect to time. Peaks may be fit, in some cases, to Gaussian and/or elliptical Gaussian functions to determine their centroid positions, intensities, widths, and/or ellipticities. Based on these parameters, peaks which are too dim, too wide, too skewed, etc. to yield satisfactory localization accuracy may be rejected in certain cases from further analysis. Peaks which are sporadic, moving, discontinuously present, etc. may also be discarded. By determining the center position of the peak, for example, using least-squares fitting to a 2-dimensional Gaussian function of the peak intensities, the location of the source of the peak (e.g., any entity or entities able to emit light, as discussed herein) can be determined. This process may be repeated as necessary for any or all of the peaks within the sample.

In another non-limiting example of a suitable imaging processing technique of the present invention, a series of images of a sample (e.g. a movie) may include a repetitive sequence of activation frames (e.g., in which the activation light is on) and imaging frames (e.g., in which the imaging light is on). For one or more of the imaging frames, fluorescent peaks can be identified and fit to Gaussian and/or elliptical Gaussian functions to determine their centroid positions, intensities, widths, and/or ellipticities. Based on these parameters, peaks that are too dim, too wide, too skewed, etc. to yield satisfactory localization accuracy may be rejected from further analysis. Peaks which are sporadic, moving, discontinuously present, etc. may also be discarded in some cases. By determining the center position of the peak, for example, using least-squares fitting to a 2-dimensional Gaussian function of the peak intensities, the location of the source of the peak (e.g., any entity or entities able to emit light, as discussed herein) can be determined. Peaks appearing in an imaging frame immediately after an activation frame can be recognized as a controlled activation event and may be color-coded according to the activation laser color, in some embodiments. This process may also be repeated as necessary for any or all of the peaks within the sample.

Other image-processing techniques may also be used to facilitate determination of the entities, for example, drift correction or noise filters may be used. Generally, in drift correction, for example, a fixed point is identified (for instance, as a fiduciary marker, e.g., a fluorescent particle may be immobilized to a substrate), and movements of the fixed point (i.e., due to mechanical drift) are used to correct the determined positions of the switchable entities. In another example method for drift correction, the correlation function between images acquired in different imaging frames or activation frames can be calculated and used for drift correction. In some embodiments, the drift may be less than about 1000 nm/min, less than about 500 nm/min, less than about 300 nm/min, less than about 100 nm/min, less than about 50 nm/min, less than about 30 nm/min, less than about 20 nm/min, less than about 10 nm/min, or less than 5 nm/min. Such drift may be achieved, for example, in a microscope having a translation stage mounted for x-y positioning of the sample slide with respect to the microscope objective. The slide may be immobilized with respect to the translation stage using a suitable restraining mechanism, for example, spring loaded clips. In addition, a buffer layer may be mounted between the stage and the microscope slide. The buffer layer may further restrain drift of the slide with respect to the translation stage, for example, by preventing slippage of the slide in some fashion. The buffer layer, in one embodiment, is a rubber or polymeric film, for instance, a silicone rubber film. Accordingly, one embodiment of the invention is directed to a device, comprising a translation stage, a restraining mechanism (e.g., a spring loaded clip) attached to the translation stage able to immobilize a slide, and optionally, a buffer layer (e.g., a silicone rubber film) positioned such that a slide restrained by the restraining mechanism contacts the buffer layer.

Multiple locations on a sample may each be analyzed to determine the entities within those locations. For example, a sample may contain a plurality of various entities, some of which are at distances of separation that are less than the wavelength of the light emitted by the entities or below the diffraction limit of the emitted light. Different locations within the sample may be determined (e.g., as different pixels within an image), and each of those locations independently analyzed to determine the entity or entities present within those locations. In some cases, the entities within each location may be determined to resolutions that are less than the wavelength of the light emitted by the entities or below the diffraction limit of the emitted light, as previously discussed.

As noted, in some embodiments, more than one type of switchable entity may be used in a sample, and the positions of each of the entities may be independently determined, in some cases, at sub-diffraction limit resolutions, e.g., to generate a multi-color image with sub-diffraction limit resolution. For instance, by repeatedly activating and deactivating particular switchable entities in a sample, the positions of a plurality of switchable entities may be determined, in some cases, to resolutions that are less than the wavelength of the light emitted by the entities or below the diffraction limit of the emitted light.

As a non-limiting example, a sample may contain two types of light emitting portions (e.g., Cy5 and Cy5.5) and two types of activation portions (e.g., Cy3 and Cy2), for a total of four (2×2) types of switchable entities: Cy5-Cy3, Cy5-Cy2, Cy5.5-Cy3, and Cy5.5-Cy2. The Cy3-containing entities can be activated by applying light at a suitable wavelength without activating the Cy2-containing entities (since different activation wavelengths are required) while light emitted by the Cy5-containing molecules can be distinguished from light emitted by the Cy5.5-containing molecules (which emits light at a different wavelength). Thus, only the Cy5-Cy3 entities will be determined, while the other entities are either not activated, or are activated but the light emitted by those entities is not used. By using the above-described techniques, the positions of the Cy5-Cy3 entities may be determined within a sample, even to resolutions that are less than the wavelength of the light emitted by Cy5. Additionally, by repeating this procedure using suitable activation and emission wavelengths, the positions of the other entities may also be determined, e.g., to sub-diffraction limit resolutions. In another example, the sample may include three (or more) types of light emitting portions (e.g., Cy5, Cy5.5 and Cy7) and/or three (or more) types of activation portions (e.g., Alexa Fluor 405, Cy2 and Cy3). Accordingly, multi-color imaging (e.g., 4 colors, 6 colors, 8 colors, 9 colors, 10 colors, 12 colors, etc.) with sub-diffraction limit resolutions may be realized.

In some embodiments of the invention, the entities may also be resolved as a function of time. For example, two or more entities may be observed at various time points to determine a time-varying process, for example, a chemical reaction, cell behavior, binding of a protein or enzyme, etc. Thus, in one embodiment, the positions of two or more entities may be determined at a first point of time (e.g., as described herein), and at any number of subsequent points of time. As a specific example, if two or more entities are immobilized relative to a common entity, the common entity may then be determined as a function of time, for example, time-varying processes such as movement of the common entity, structural and/or configurational changes of the common entity, reactions involving the common entity, or the like. The time-resolved imaging may be facilitated in some cases since a switchable entity can be switched for multiple cycles, each cycle give one data point of the position of the entity.

Another aspect of the invention is directed to a computer-implemented method. For instance, a computer and/or an automated system may be provided that is able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. The processing steps may also be recorded onto a machine-readable medium in some cases.

Still another aspect of the invention is generally directed to a system able to perform one or more of the embodiments described herein. For example, the system may include a microscope, a device for activating and/or switching the entities to produce light having a desired wavelength (e.g., a laser or other light source), a device for determining the light emitted by the entities (e.g., a camera, which may include color-filtering devices, such as optical filters), and a computer for determining the spatial positions of the two or more entities. In some cases, mirrors (such as dichroic mirror or a polychroic mirror), prisms, lens, diffraction gratings, or the like may be positioned to direct light from the light source. In some cases, the light sources may be time-modulated (e.g., by shutters, acoustic optical modulators, or the like). Thus, the light source may be one that is activatable and deactivatable in a programmed or a periodic fashion. In one embodiment, more than one light source may be used, e.g., which may be used to illuminate a sample with different wavelengths or colors. For instance, the light sources may emanate light at different frequencies, and/or color-filtering devices, such as optical filters or the like may be used to modify light coming from the light sources such that different wavelengths or colors illuminate a sample.

In some embodiments, a microscope may be configured so to collect light emitted by the switchable entities while minimizing light from other sources of fluorescence (e.g., "background noise"). In certain cases, imaging geometry such as, but not limited to, a total-internal-reflection geometry a spinning-disc confocal geometry, a scanning confocal geometry, an epi-fluorescence geometry, etc., may be used for sample excitation. In some embodiments, a thin layer or plane of the sample is exposed to excitation light, which may reduce excitation of fluorescence outside of the sample plane. A high numerical aperture lens may be used to gather the light emitted by the sample. The light may be processed, for example, using filters to remove excitation light, resulting in the collection of emission light from the sample. In some cases, the magnification factor at which the image is collected can be optimized, for example, when the edge length of each pixel of the image corresponds to the length of a standard deviation of a diffraction limited spot in the image.

In some cases, a computer may be used to control excitation of the switchable entities and the acquisition of images of the switchable entities. In one set of embodiments, a sample may be excited using light having various wavelengths and/or intensities, and the sequence of the wavelengths of light used to excite the sample may be correlated, using a computer, to the images acquired of the sample containing the switchable entities. For instance, the computer may apply light having various wavelengths and/or intensities to a sample to yield different average numbers of activated switchable elements in each region of interest (e.g., one activated entity per location, two activated entities per location, etc). In some cases, this information may be used to construct an image of the switchable entities, in some cases at sub-diffraction limit resolutions, as noted above.

In other aspects of the invention, the systems and methods described herein may also be combined with other imaging techniques known to those of ordinary skill in the art, such as high-resolution fluorescence in situ hybridization (FISH) or immunofluorescence imaging, live cell imaging, confocal imaging, epi-fluorescence imaging, total internal reflection fluorescence imaging, etc.

The following are incorporated herein by reference: U.S. Provisional Patent Application Ser. No. 60/836,167, filed Aug. 7, 2006, entitled "Sub-Diffraction Image Resolution"; and U.S. Provisional Patent Application Ser. No. 60/836,170, filed Aug. 8, 2006, entitled "Sub-Diffraction Image Resolution."

The following examples are intended to illustrate certain embodiments of the present invention, but do not exemplify the full scope of the invention.

EXAMPLES

This example shows a high-resolution optical microscopy, stochastic optical reconstruction microscopy ("STORM"), in which a fluorescence image is constructed from high-accuracy localization of individual fluorescent entities ("fluorophores") that are switched on and off using light of different colors, in accordance with one embodiment of the invention. The STORM imaging process in this example includes a series of imaging cycles (FIG. 1A). In each cycle, a fraction of the fluorophores in the field of view are switched on or activated, such that each of the active fluorophores is optically resolvable from the rest, i.e. their images are not overlapping. This allows the position of these fluorophores to be determined with high accuracy. Repeating this process for multiple cycles, each causing a stochastically different subset of fluorophores to be turned on or activated, enables the positions of many fluorophores to be determined and thus an overall image to be reconstructed. In these examples, an imaging resolution of approximately 20 nm is demonstrated, an improvement of more than 10 times over the resolution of conventional fluorescence microscopy, using a simple total-internal-reflection fluorescence microscope, low-power continuous-wave lasers, and a photoswitchable cyanine dye.

FIG. 1A shows that a STORM imaging sequence using a hypothetical hexameric object labeled with fluorophores can be switched between a fluorescent and a dark state by a green and a red laser, respectively. In this non-limiting illustration, all fluorophores were first switched "off" to the dark state ("deactivated") by a strong red laser pulse. In each imaging cycle, a green laser pulse was used to switch on ("activate") only a fraction of the fluorophores to give an optically resolvable set of active fluorophores. Next, under red illumination ("image"), these molecules emitted fluorescence until they were switched off, allowing their positions (indicated by white crosses) to be determined with relatively high accuracy. The overall image was then reconstructed from the fluorophore positions obtained from multiple imaging cycles.

Figure 1B:
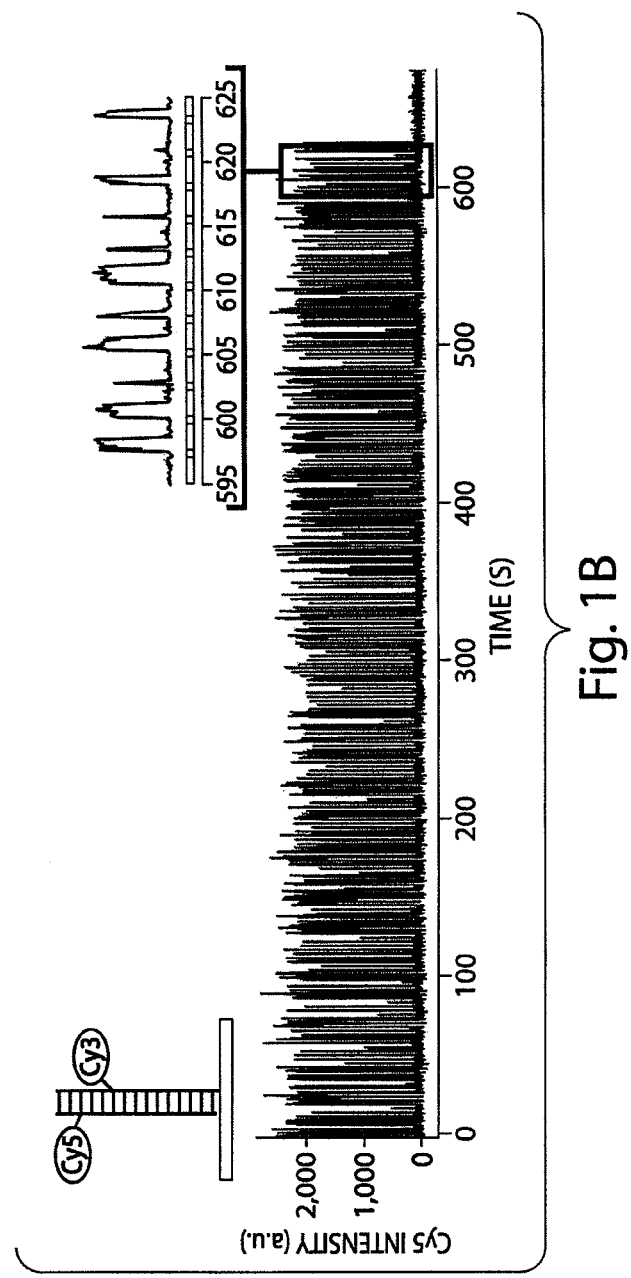

Cyanine dye, Cy5, can be switched between a fluorescent and a dark state in a controlled and reversible manner by light of different wavelengths. Red laser light that produces fluorescent emission from Cy5 can also switch the dye to a stable dark state. Exposure to green laser light converts Cy5 back to the fluorescent state, but the recovery rate may depend in some cases on the close proximity of a secondary dye, Cy3. The Cy3-Cy5 dye pair can also be referred to as a switch. Under illumination conditions allowing single-molecule detection, it was found that such a switch, when attached or immobilized to nucleic acids or proteins, can be cycled on and off hundreds of times before permanent photobleaching occurs (FIG. 1B and FIG. 4). In FIG. 1B, a red laser (633 nm, 30 W/cm$^2$) was used to excite fluorescence (black line) from Cy5 and to switch Cy5 to the dark state. A green laser (532 nm, 1 W/cm$^2$) was used to return Cy5 to the fluorescent state. The alternating red and green line indicates the laser excitation pattern. In some cases, the recovery rate of Cy5 appeared to depend on the close proximity of Cy3.

FIG. 4 shows goat anti-mouse secondary antibody labeled with the cyanine switch exhibits photoswitching behavior similar to switch-labeled DNA. The antibody was labeled with Cy3 and Cy5 (see below) and bound to a quartz slide coated with unlabeled mouse anti-transferrin primary antibody. The trace shows the Cy5 fluorescence intensity detected from a single labeled antibody as it switched on and off until permanent photobleaching occurs after about 230 seconds. The sample was excited with a sequence of alternating green and red laser pulses (0.5 s green followed by 2 s red).

Figure 8A:
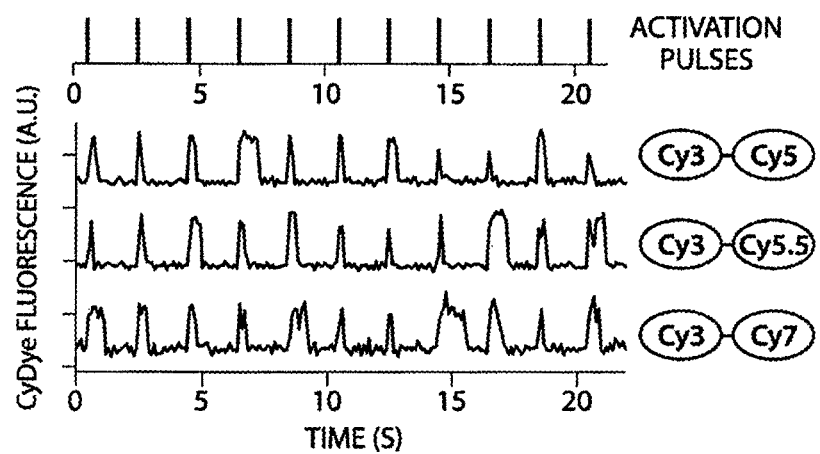
FIGS. 8A-8B illustrate various photoswitchable entities, according to certain embodiments of the invention.
Figure 8B:
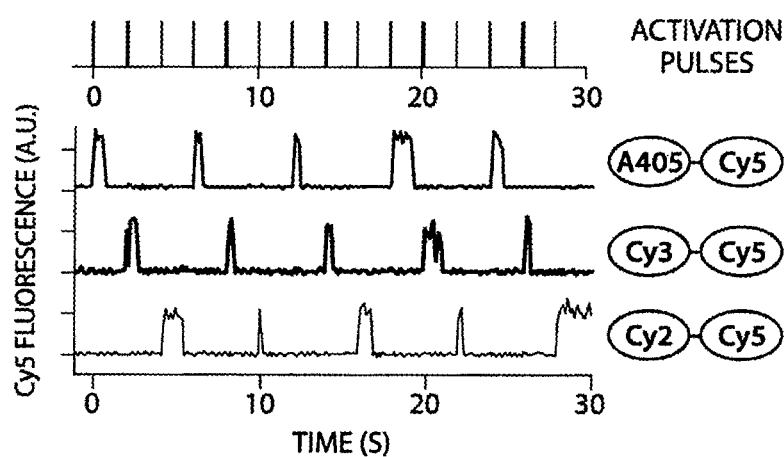
Figure 9A:
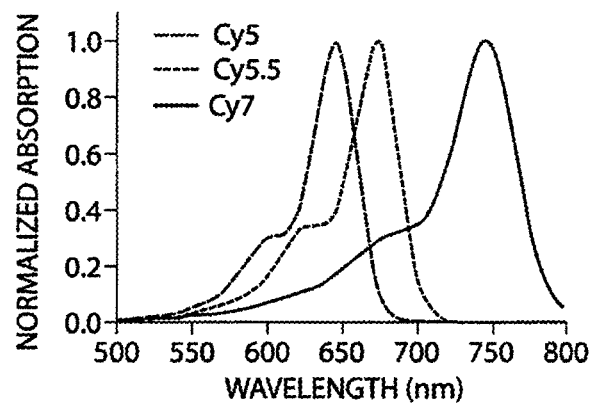
FIGS. 9A-9C illustrate absorption and emission spectra of various moieties, according to certain embodiments of the invention.
Figure 9B:
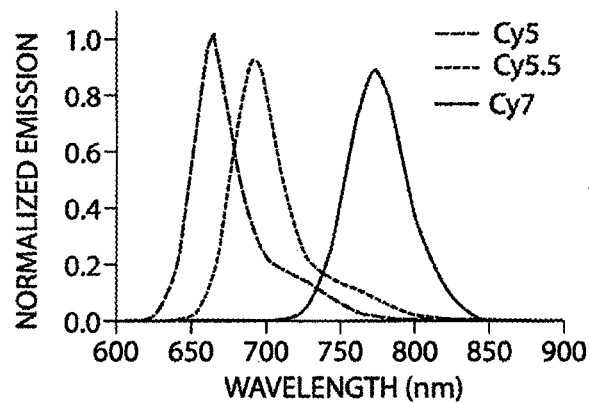
Figure 9C:
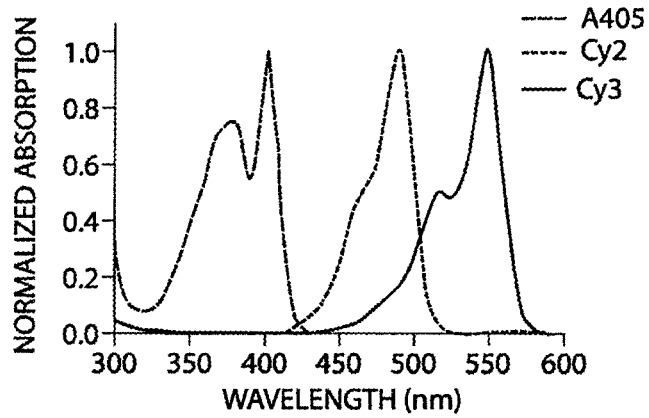

Other photoswitchable dye pairs can be constructed using similar principles. For instance, in addition to Cy5, Cy5.5, Cy7, and Alexa Fluor 647 can also be switched between a fluorescent and a dark state in a controlled and reversible manner by light of different wavelengths. When paired with Cy3, upon illumination with a red laser (633 nm or 657 nm), each of these four dyes (Cy5, Cy5.5, Cy7, and Alexa Fluor 647) was initially fluorescent and then quickly switched into a non-fluorescent, dark state. A brief exposure to a green laser pulse (532 nm) led to reactivation of these dyes back to the fluorescent state (see FIGS. 8A and 9). Furthermore, different activating portion can be used to activate the same emitting portion in some cases. For instance, using Cy5 as an example for the emitting portion, Cy3, Cy2, and Alexa Fluor 405 could be paired with Cy5. Upon illumination with a red laser (633 nm or 657 nm), Cy5 was observed to be quickly switched into the dark state. In this example, the reactivation of Cy5 required different colored lasers corresponding to the absorption wavelength of the activator (FIGS. 8B and 9). The Alexa 405-Cy5 pair was efficiently activated by a violet laser (405 nm), but appeared to be less sensitive to blue (457 nm) and green (532 nm) lasers. Similarly, the Cy2-Cy5 pair was more sensitive to the blue light than to violet or green light, whereas the Cy3-Cy5 pair was appeared more sensitive to the green laser.

Examples of activator portions include, but are not limited to, Alexa Fluor 405, Alexa Fluor 488, Cy2, Cy3, Cy3.5, or Cy5. Examples of light-emitting portions include, but are not limited to, Cy5, Cy5.5, Cy7, Alexa Fluor 647, Alexa Fluor 680, or Alexa Fluor 700. These may be linked together to form photoswitchable entities such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, or Cy7-Cy5.

Figure 2A:
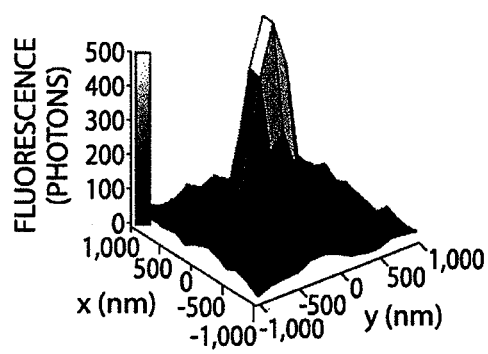
FIGS. 2A-2D illustrate the localization of molecular entities according to another embodiment of the invention.
Figure 2B:
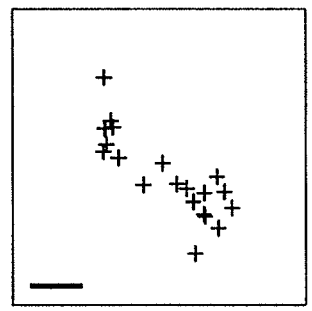
Figure 2C:
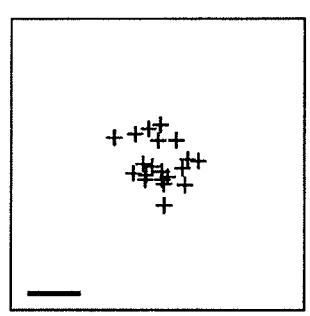
Figure 2D:
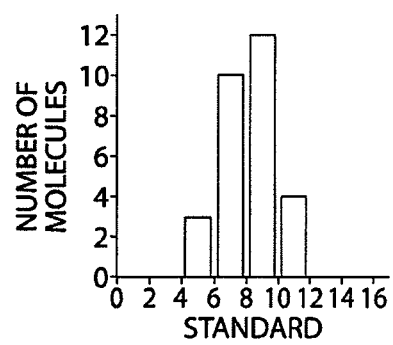

In this example, the concept of STORM is shown using the Cy5-053 switch, but any suitably optically switched fluorophores could also be used. The resolution of STORM may be limited in some cases by the accuracy with which individual switches can be localized during a switching cycle. As an example of determining the localization accuracy, a switch was attached or immobilized to a short double-stranded DNA, which was surface-immobilized at low density so that single switches were resolvable. These switches were periodically cycled on and off using green and red laser light, and the red laser also served to excite fluorescence from Cy5. No fluorescence from Cy3 was recorded in this process. The high localization accuracy of individual switches during each switching cycle defining the intrinsic resolution of STORM is shown in FIG. 2. The fluorescence image from a single switch gave a point-spread function shown in FIG. 2A. The point spread function (PSF) of the emission from a single switch on DNA during a single switching cycle. A Gaussian fit to this image (not shown) was used to localize the centroid position of the PSF, indicating the position of the switch. The positions determined from multiple switching cycles showed a substantial spread (FIG. 2B), which was significantly reduced by correcting for sample drift over the course of the experiment (FIG. 2C, see below for additional details). FIGS. 2B and 2C show the centroid positions of an individual switch determined in 20 successive imaging cycles before (FIG. 2B) and after (FIG. 2C) correction for sample drift. The scale bars are 20 nm. The standard deviation of the drift-corrected positions obtained from 20 imaging cycles was on average 8 nm for individual switches (FIG. 2D). FIG. 2D shows a histogram of the standard deviation of centroid positions. The standard deviation is determined as $(\sigma_x+\sigma_y)/2$ ((sigma-x+sigma-y)/2) for each switch using 20 imaging cycles, where $\sigma_x$ (sigma-x) and $\sigma_y$ (sigma-y) are the standard deviations of the centroid positions in the x and y dimensions. This histogram was constructed from 29 switches. This value gave a measure of the uncertainty in the localization of a single switch per imaging cycle. Correspondingly, the experimentally measured spread of switch positions follows a Gaussian distribution with a FWHM of 18 nm, as expected from the 8 nm standard deviation (FIG. 5). Therefore, under these imaging conditions, two switches separated by 20 nm could be resolved.

Figure 5A:
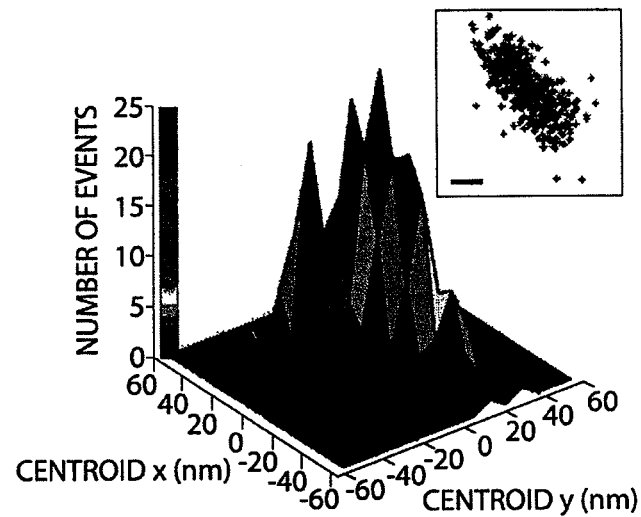
FIGS. 5A-5B illustrate drift correction in another embodiment of the invention.
Figure 5B:
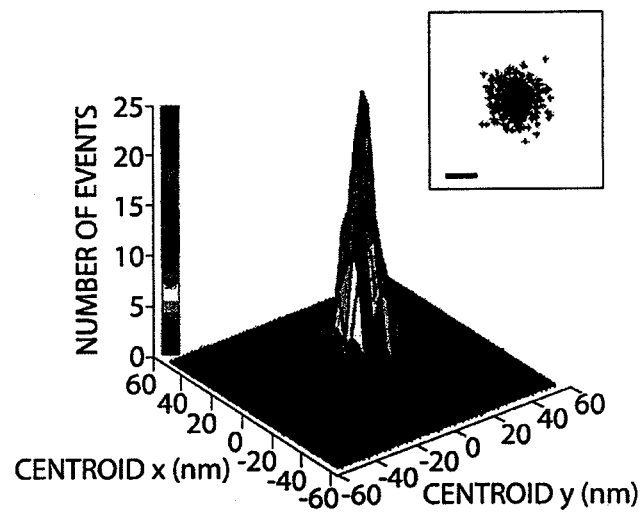

FIG. 5 shows the superimposed position distributions of 29 individual switches before (FIG. 5A) and after (FIG. 5B) correction for stage drift. The scale bar is 20 nm. To obtain these distributions, the image of each switch during a given imaging cycle was fit to a two-dimensional Gaussian function, yielding the centroid position of each switch during that cycle. Twenty imaging cycles were carried out, giving twenty measured positions per switch. The position data for each switch were realigned so that the average position of each switch was at the origin, and the measurements from different switches were then superimposed to give the overall position distribution shown in the insets. The main plots are histograms of these centroid positions. The uncorrected distribution is fairly broad and skewed asymmetrically. After correction for stage drift using fiducial markers (see below) the distribution become significantly narrower. The fit of the drift-corrected histogram to a Gaussian gave a full width at half-maximum of 18±2 nm.

Figure 3A:
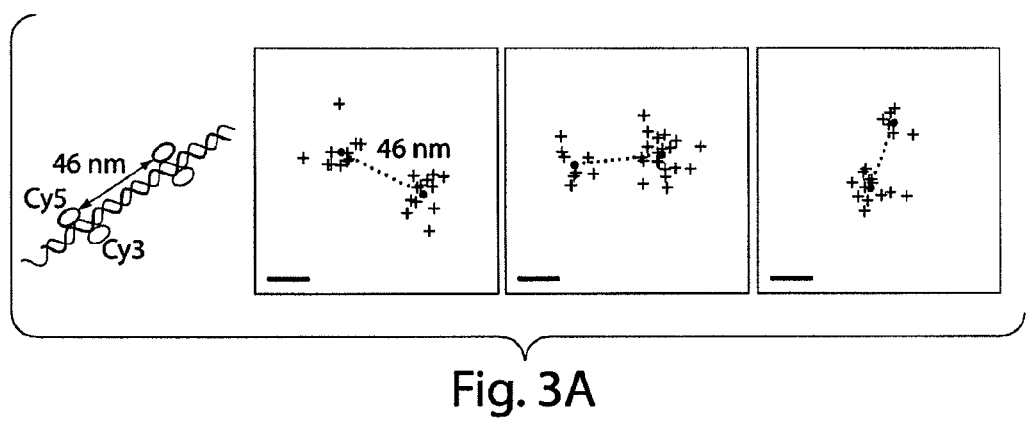
FIGS. 3A-3D illustrate the sub-diffraction limit localization of photoswitchable molecular entities according to yet another embodiment of the invention.
Figure 3B:
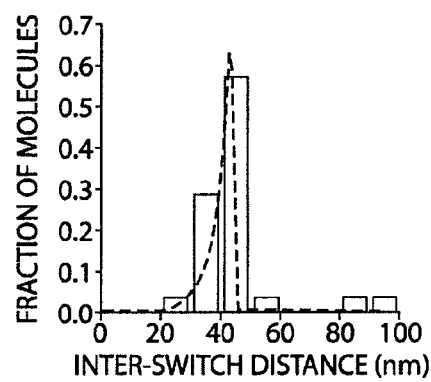
Figure 3C:
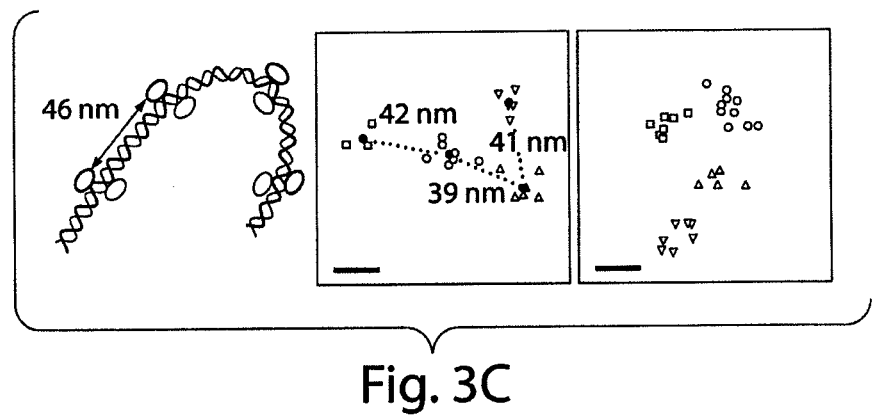

To demonstrate the capability of STORM to resolve fluorescent molecules in close proximity, standard samples of linear, double-stranded DNA labeled were constructed with multiple switches separated by a well-defined number of base pairs (see methods, below, for details). The DNA strands were also labeled with multiple biotins and attached to a high-density streptavidin layer (see below), increasing the likelihood of multiple attachments between the DNA and the surface so that the DNA was immobilized in the plane. DNA strands were first examined containing two switches separated by 135 base-pairs (FIG. 3A and FIG. 6), corresponding to a length of 46 nm along the DNA contour. A STORM image obtained using the imaging procedure described above (see below for details) showed two clusters of measured switch positions, indicating that the two switches were well-resolved (FIG. 3A). This image shows two separated clusters of measured switch positions (crosses), each corresponding to a single switch. The center-of-mass position of each cluster is marked by a dot. The inter-switch distances are 46 nm, 44 nm and 34 nm for these three examples. The scale bars are 20 nm. The distance between the centers of the two clouds had a mean value of 41 nm (FIG. 3B), in quantitative agreement with the theoretical mean (40 nm) determined using the known contour and persistence lengths of the DNA sample (see below). FIG. 3B shows a comparison between the inter-switch distances measured using STORM (grey column) and the predicted distance distribution considering the flexibility of DNA (dashed line). FIG. 3C shows STORM images of four switches attached to a double-stranded DNA, pair-wise separated by a contour length of 46 nm. The measured switch positions were clustered by an automated algorithm (see below for details) and different clusters are indicated by different symbols. The scale bars are 20 nm.

Figure 6:
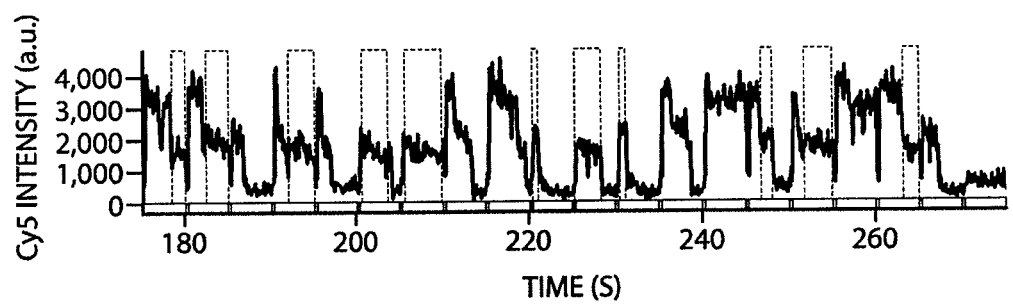
FIG. 6 illustrates the repeated switching of two molecular switches, in yet another embodiment of the invention.
Figure 7A:
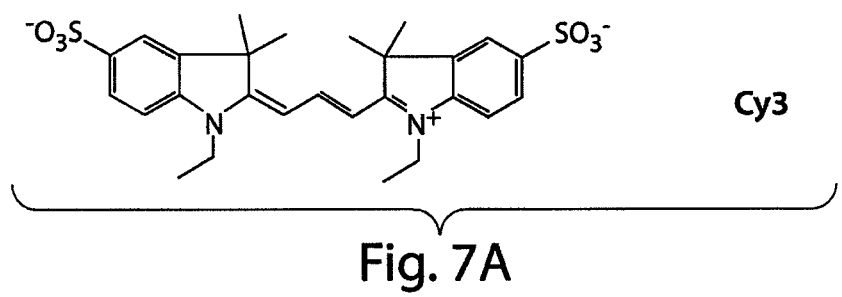
FIGS. 7A-7E respectively illustrate the structures of Cy3, Cy5, Cy5.5, Cy7, and an example of a linked Cy3-Cy5 moiety.
Figure 7B:
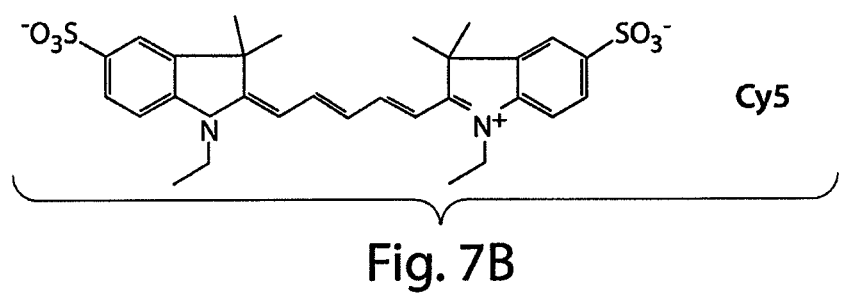
Figure 7C:
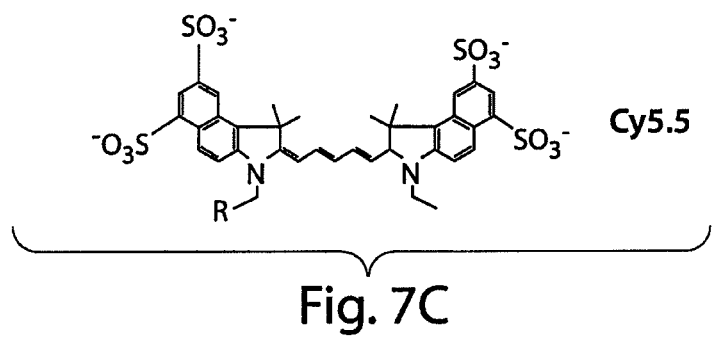
Figure 7D:
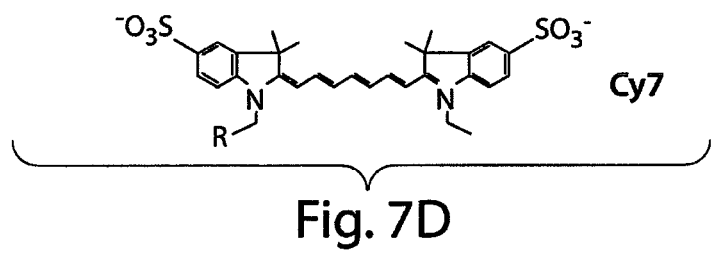
Figure 7E:
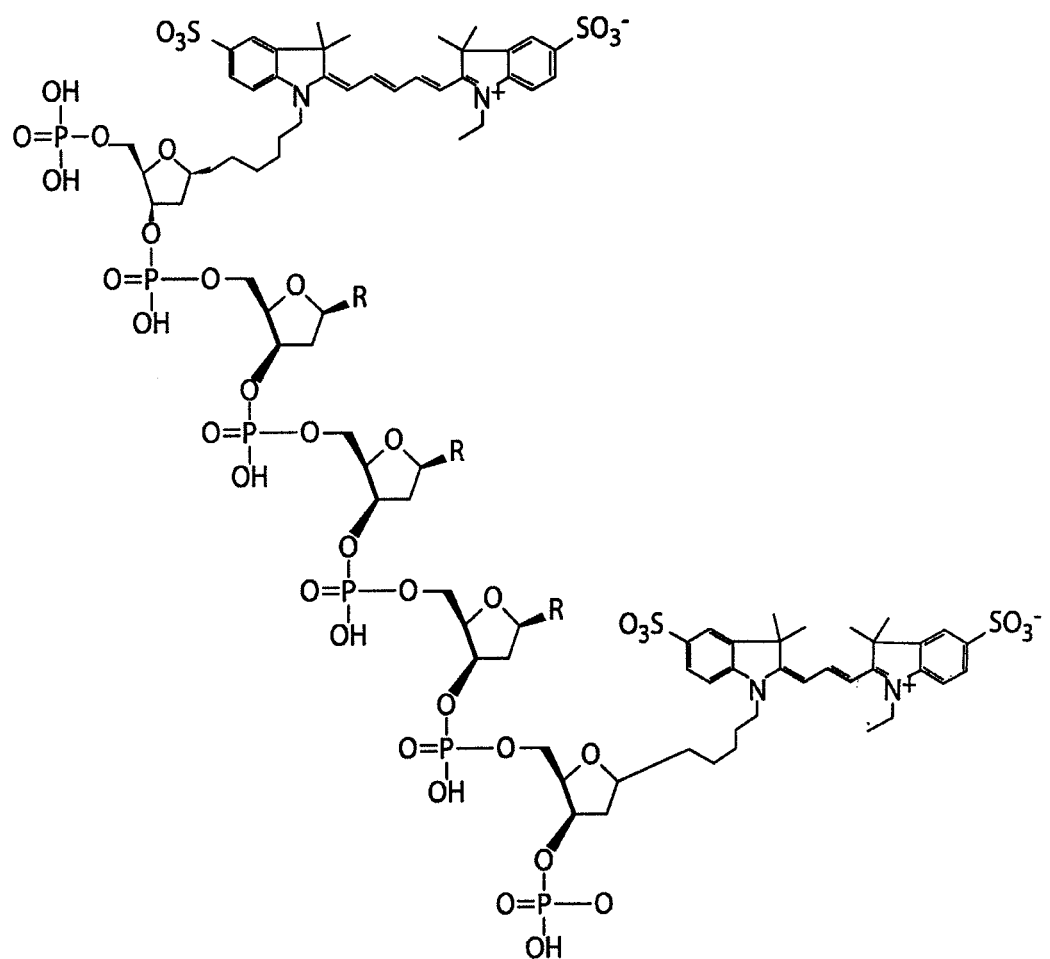

FIG. 6 is an excerpt of a fluorescence trace (black line) showing the cycling of Cy3-Cy5 switches separated by a contour length of 46 nm on dsDNA (see also FIG. 3A). Each switching cycle lasted for 5 seconds and included a brief green pulse (underlying tick marks) to activate one or two switches followed by a long red exposure (underlying bar) to excite Cy5 fluorescence and return the switches to the off state. In cycles when one switch is activated (e.g. 225-230 seconds), a single intensity level was apparent before the return to the dark state. In cycles where two switches are activated (e.g. 245-250 seconds), a "staircase" with two decreasing levels corresponding to the sequential switching off of each dye is observed. Regions where only a single switch is on and all of the peak quality criteria are satisfied (see below) were used for single-switch localization.

Longer DNA samples labeled with four switches evenly separated by 46 nm along the contour were also imaged. The STORM images revealed four clusters of switch positions following a bent contour consistent with the persistence length of DNA and the engineered separation between the switches. These results indicated that STORM can image biological samples with sub-diffraction limit resolution and that features separated by 40 nm are well within the resolving power.

Figure 3D:
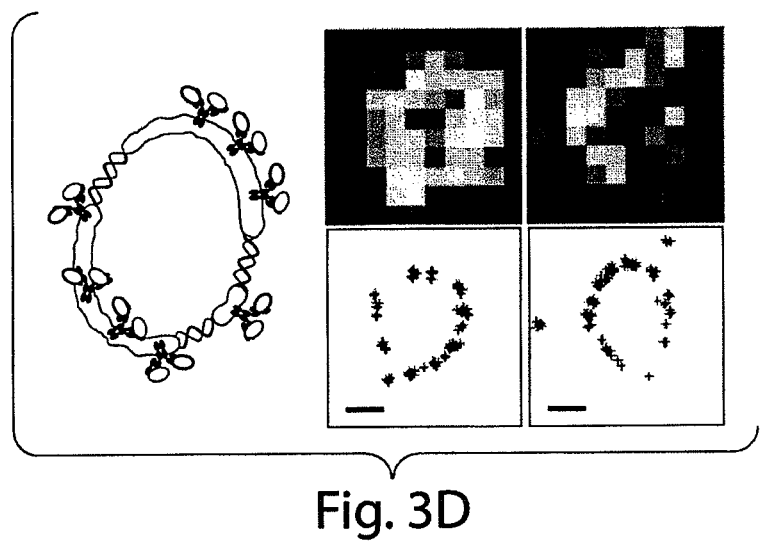

One advantage of STORM is its ability to localize a large number of switches within a diffraction-limited spot by cycling the switches on and off in a controlled manner, allowing this to be used as a general biological imaging technique. To demonstrate this capability, circular DNA plasmids were prepared and coated with RecA protein and imaged using indirect immunofluorescence with switch-labeled secondary antibody (FIG. 3D, see methods, below, for details). Here the photoswitch comprise of Cy3 and Cy5. Cy3 serve as the activating portion and Cy5 serve as the light-emitting portion. STORM images of the RecA filaments revealed their circular structure with greatly increased resolution when compared with conventional wide-field images. Parts of the filament appear to be unlabeled or kinked, which may correspond to regions of the plasmid that remain uncoated by RecA. In FIG. 3D, the top panels show indirect immunofluorescence images with switch-labeled secondary antibody taken by a total internal reflection microscope. The bottom panels are the reconstructed STORM images of the same filaments. The scale bars are 300 nm.

The presence of multiple types of photoswitchable pairs of light emitting portion and activating portion may also allow multi-color STORM imaging, e.g., as described herein. This example uses a selective activation scheme as an initial demonstration of multicolor STORM imaging. Three different DNA constructs labeled with Alexa 405-

Figure 12A:
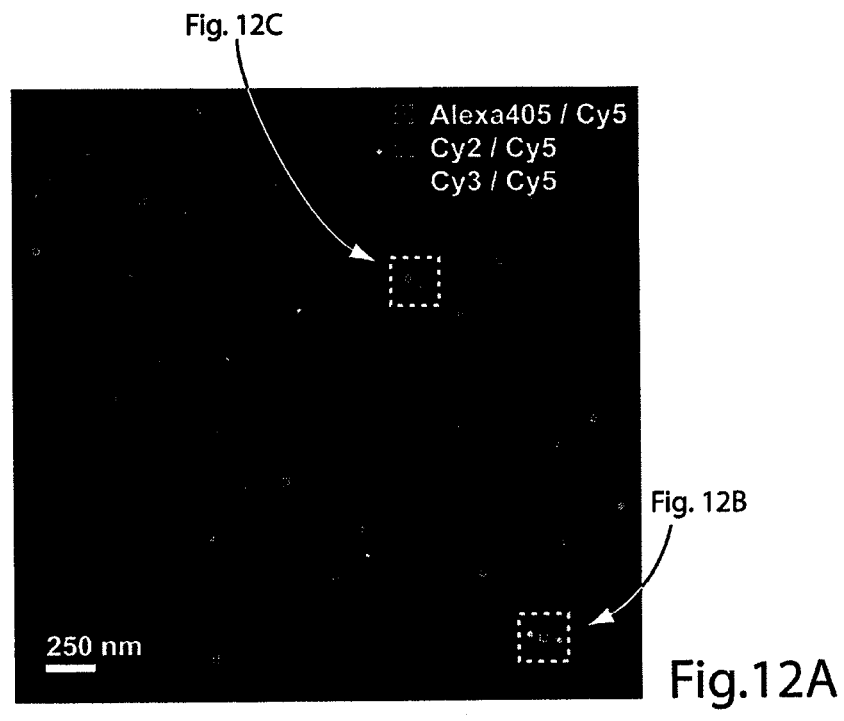
FIGS. 12A-12F illustrate multi-color, sub-diffraction limit localization of multiple types of photoswitchable molecular, entities according to yet another embodiment of the invention.
Figure 12B:
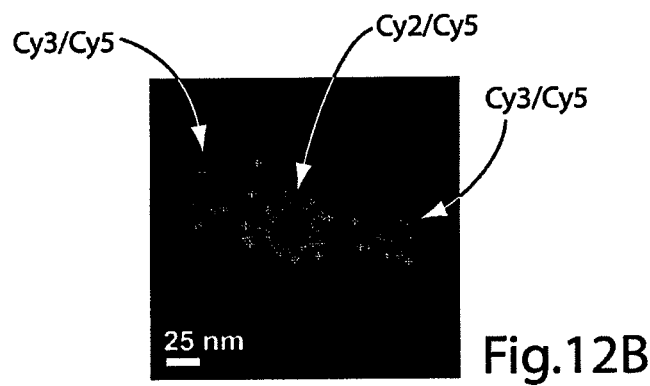
Figure 12C:
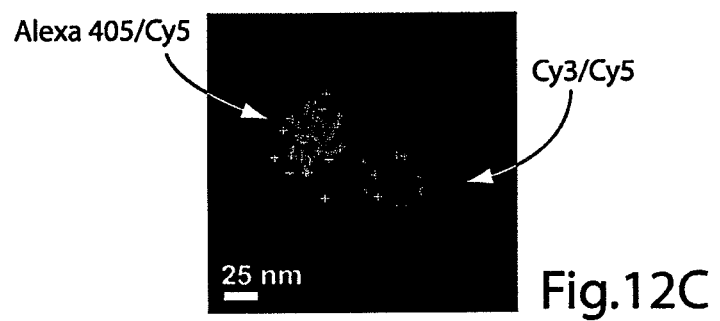
Figure 12D:
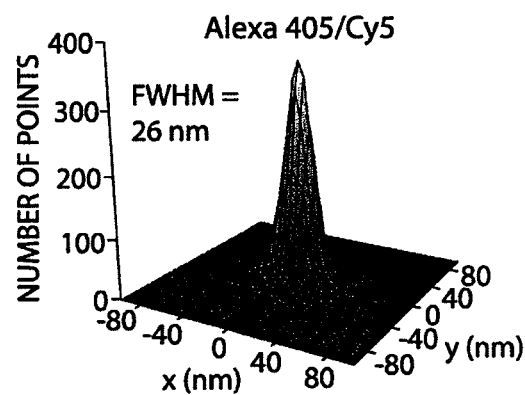
Figure 12E:
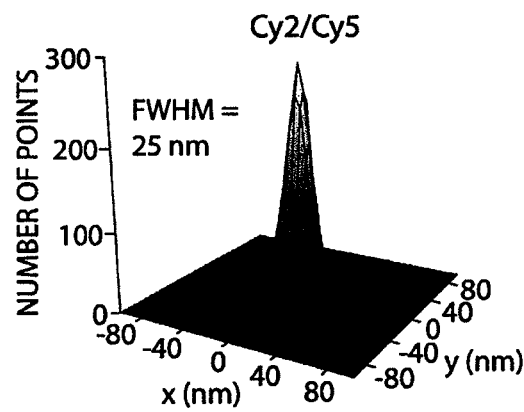
Figure 12F:
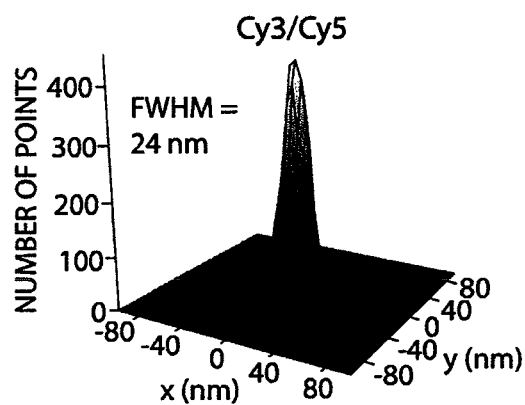

Cy5, Cy2-Cy5, or Cy3-Cy5 were mixed and immobilized on a microscope slide at a high surface density such that individual DNA molecules could not be resolved in a conventional fluorescence image. To generate a STORM image, the sample was first exposed to a red laser (633 nm) to switch off nearly all Cy5 dyes in the field of view. The sample was then periodically excited with a sequence of violet (405 nm), blue (457 nm), and green (532 nm) laser pulses, each of which activated a sparse, optically resolvable subset of fluorophores. In between activation pulses, the sample was imaged with the red laser. The image of each activated fluorescent spot was analyzed to determine its centroid position (referred to as a localization), and a color was assigned according to the preceding activation pulse. As the same imaging laser and detection channel were used for all three dye pairs, there was no need for correction of chromatic aberration. After thousands of activation cycles, a STORM image was constructed by plotting all of the colored localizations (FIGS. 12A-12C). The STORM image showed separated clusters of localizations. Each cluster corresponded to an individual DNA molecule and resulted from the repetitive localization of a single Cy5 molecule over multiple switching cycles. The majority of the localizations within each cluster displayed the same color, identifying the type of activator dye present on the DNA. There were two origins of crosstalk between colors that were identified: false activation by laser pulses of incorrect colors and non-specific activation by the red imaging laser, but both effects were quantitatively small. The localizations within each cluster approximately follow a Gaussian distribution with a full-width-half-maximum (FWHM) of 26±1 nm, 25±1 nm, and 24±1 nm for the three color channels (FIGS. 12D-12F), suggesting an imaging resolution of ~25 nm. This resolution is lower than the theoretical limit predicted from the number of photons detected.

Figure 10A:
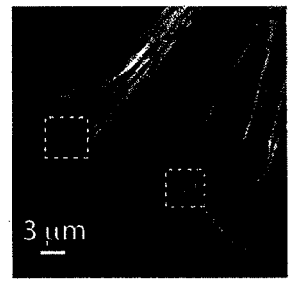
FIGS. 10A-10F illustrate sub-diffraction limit imaging of cells with photoswitchable entities, according to certain embodiments of the invention.
Figure 10B:
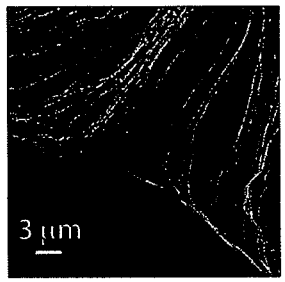
Figure 10C:
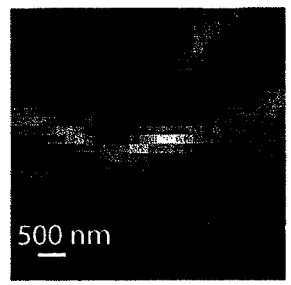
Figure 10D:
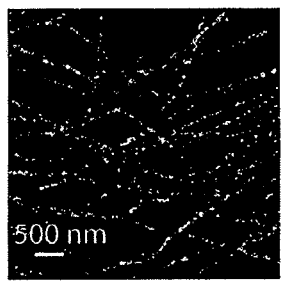
Figure 10E:
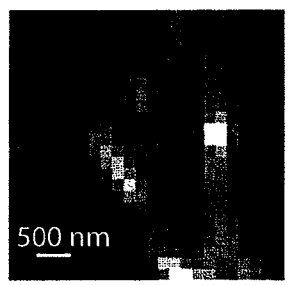
Figure 10F:
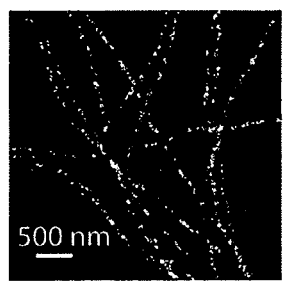

STORM imaging can also be performed on cell samples. To demonstrate this capability, in this example, single-color immunofluorescence imaging of microtubules, which are filamentous cytoskeleton structures important for many cellular functions, were performed. BS-C-1 cells were fixed and immunostained with primary antibodies against microtubules and then with a switch-labeled secondary antibody. Here, the photoswitch used comprised Cy3 and Alexa Fluor 647, with Cy3 serving as the activating portion and Alexa Fluor 647 serving as the light-emitting portion. The STORM image showed a drastic improvement in the resolution of the microtubule network as compared to the conventional fluorescence image (FIG. 10). FIGS. 10A, 10C, and 10E are conventional images of microtubules in regions of the cell, shown at different scales, and FIGS. 10B, 10D, and 10F are STORM images of the same regions. In the regions where microtubules were densely packed and undefined in the conventional image, individual microtubule filaments were resolved by STORM (FIGS. 10C-F). Whole-cell STORM images, including ~$10^6$ single-molecule localizations, were acquired in 2 to 30 minutes. Super-resolution microtubule structures began to emerge after only about 10 to 20 seconds of STORM imaging, although this was not optimized. The effective imaging resolution was affected both by the intrinsic dye localization accuracy and the size of the antibody labels. Improvement in the effective resolution may be achieved by using direct immunofluorescence staining with dye-labeled primary antibodies or Fab fragments.

Figure 11A:
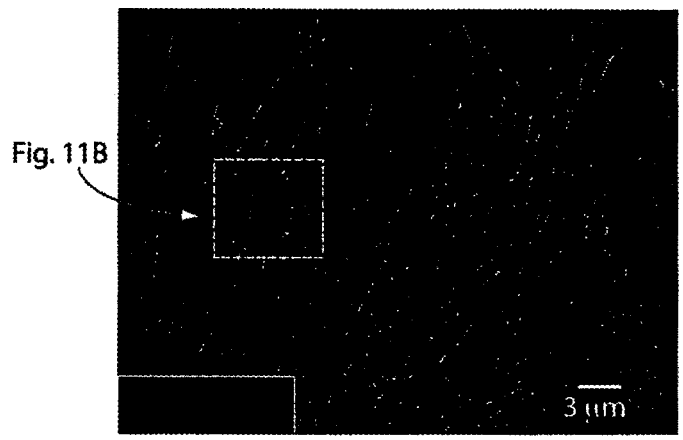
FIGS. 11A-11C illustrate multi-color, sub-diffraction limit imaging of cells with photoswitchable entities, according to certain embodiments of the invention.
Figure 11B:
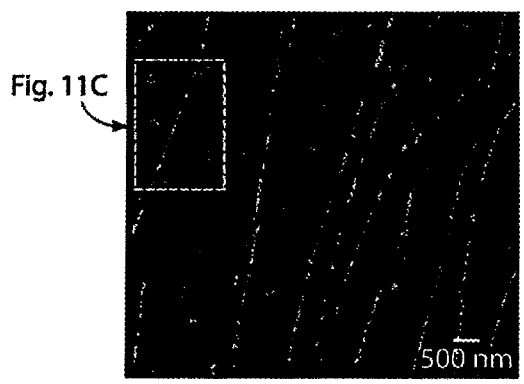
Figure 11C:
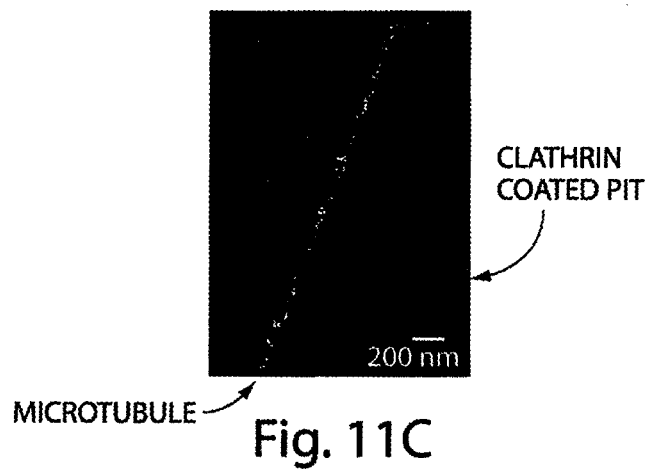

Using different photoswitchable pairs, multi-color STORM imaging can also be performed on cell samples. To demonstrate this capability, microtubules and clathrin-coated pits (CCPs), cellular structures used for receptor-mediated endocytosis, were simultaneously imaged. The microtubules and clathrin were immunostained with primary antibodies and then with switch-labeled secondary antibodies. Here, the photoswitches comprised Cy2 and Alexa Fluor 647 for microtubule imaging, and Cy3 and Alexa Fluor 647 for clathrin imaging, with Cy2 or Cy3 serving as the activating portion and Alexa Fluor 647 serving as the light-emitting portion. The 457 nm and 532 nm lasers were used to selectively activate the two pairs. Crosstalk between the two color channels due to false and non-specific activations were subtracted from the image after statistical analysis. FIG. 11 shows two-color super-resolution STORM images of microtubules and clathrin-coated pits. FIG. 11 shows the two-color STORM image presented at different scales. The green channel (457 nm activation) revealed filamentous structures for microtubules (long thin structures in these images). The red channel reveals predominantly spherical structures in these images, which were the clathrin-coated pits and vesicles.

In summary, this example demonstrates that STORM is capable of imaging biological structures with sub-diffraction limit resolution. The resolution of the technique is not limited to the wavelength of light. For the Cy3-Cy5 switch, approximately 3,000 photons were detected per switching cycle, independent of red laser intensity (data not shown), predicting a theoretical localization accuracy of 4 nm. The difference between this theoretical prediction and the measured accuracy of 8 nm is relatively small, and the discrepancy may be due to imperfect correction of stage drift and aberration due to focus drift in the measurements. This measured localization accuracy corresponds to an imaging resolution of approximately 20 nm (full width half maximum, FWHM). Indeed, fluorescent switches separated by ~40 nm were readily resolved (FIG. 3).

The cyanine switches could be turned on and off reliably for hundreds of cycles before photobleaching, allowing STORM to be used for resolving structures with many fluorophores in a potentially time-resolved manner. The circular structure of RecA filaments containing 10-20 switches and microtubule and clathrin-coated pits structures in cells could be resolved in a few minutes or less. The imaging speed may be improved, for instance, by increasing the switching rate through stronger excitation or fluorophores with faster switching kinetics, by using a camera with a faster frame rate, by using a fast camera reading scheme, such as binning pixels or only reading out a fraction of the pixels, or by other technique. STORM is thus a valuable tool for high-resolution imaging of biological or nonbiological samples. The STORM concept is also applicable to other photoswitchable fluorophores and fluorescent proteins, which will potentially allow high-resolution live-cell imaging with endogenous labels, and any other imaging applications in which sub-diffraction limit image resolution is desired.

For additional details and examples, see W. M. Bates, et al., "Multicolor Super-resolution Imaging with Photo-switchable Fluorescent Probes" Science (in press), or M. J. Rust, et al., "Sub-diffraction-limit imaging by stochastic reconstruction optical microscopy (STORM)," *Nature Methods* 3, 793-795 (2006).

Following are methods useful in the above description.
Preparation of Switch-Labeled DNA Constructs.
Biotinylated and/or amine-modified DNA oligonucleotides ("oligos") were purchased, PAGE purified, from Operon. Amine-modified oligos were labeled with amine reactive Cyanine dyes (Amersham Bioscience) or Alexa dyes (Invitrogen) post-synthetically following the protocol provided by the manufacturer. The dye-labeled oligos were purified using reverse phase HPLC. Complementary strands of DNA were annealed to form biotinylated double-stranded DNA (dsDNA) by mixing equimolar amounts of the two complementary strands in 10 mM Tris-Cl (pH 7.5), 50 mM NaCl, heating to 90° C. for two minutes, and then allowing the mixture to cool to room temperature in a heat block over a period of one hour.

Biotinylated dsDNA of varying lengths having an intra-switch distance of 135 bp were constructed by annealing complimentary oligos as described above to form three different 45 bp dsDNA segments denoted A, B, and C, followed by a ligation reaction. The oligos were designed with specific sticky ends which only permit A to ligate to B, B to ligate to C and C to ligate to A, reading in the 5' to 3' direction. One oligo (A) contained amine-reactive sites three base pairs apart on opposite strands which were specifically labeled with Cy3 and Cy5 prior to annealing to form the optical switch. Oligos B and C contain two internal biotin modifications per strand to facilitate multivalent linkage to the streptavidin surface. After annealing, the oligos were mixed at equal concentrations and ligated overnight using T4 ligase (New England Biolabs). The resulting ligation product was purified on a 1.5% agarose gel to select bands containing the desired concatamerized dsDNA length.

Preparation of Switch-Labeled Antibodies.

Goat antimouse IgG secondary antibodies (Abcam or Invitrogen) and goat anti-rabbit antibody (Abcam) were labeled non-specifically with amine-reactive Cy2 or Cy3 (to serve as an activating portion) and Cy5 or Alexa 647 (to serve as a light-emitting portion). The average dye-to-antibody ratio was ~2:1 for Cy3 and ~0.1:1 for Cy5 in the case of Rec A imaging. In the case of microtubule and clathrin imaging, dye-to-antibody ratio was ~2:1 for Cy3 or Cy2 and ~0.4:1 for Alexa Fluor 647. Various Cy5-to-antibody or Alexa 647-to-antibody ratios may be used for STORM imaging, for example, ratios up to or greater than 0.8. Various Cy3-to-antibody ratios and Cy2-to-antibody ratios can also be used for efficiently STORM imaging. The imaging quality appears not to be very sensitive the Cy3 (or Cy2)-to-antibody ratio. These labeling ratios were chosen to minimize the fraction of antibodies labeled with more than one Cy5 molecule, due to the inefficient switching observed for antibodies labeled with multiple Cy5. The presence of more than one Cy3 molecule on a single antibody did not interfere with switching. With this labeling ratio, a significant fraction of the secondary antibody did not carry Cy5, and were not observed. This lower density of labels is typically not a problem for indirect immunofluorescence imaging and, in particular, did not prevent resolution of the circular structure of the RecA-plasmid filaments or microtubules.

Preparation of RecA Filaments.

Biotinylated RecA was prepared by reacting purified recombinant RecA (New England Biolabs) with amine-reactive biotin-XX (Invitrogen) in 0.1 M carbonate buffer at pH 8.3. The resulting biotinylated protein was purified on a NAP-5 size exclusion column (Amersham). RecA filaments were formed on ΦXRF-II (Phi-XRF) plasmid DNA (New England Biolabs) by incubating RecA (25% biotinylated: 75% unbiotinylated, concentration of 80 micrograms/mL) with plasmid DNA (2 micrograms/mL) in 10 mM Tris buffer at pH 7.0, 100 mM NaCl, 7 mM $MgCl_2$, and 0.8 mg/mL ATP-γ-S (ATP-gamma-S) for 1 hour at 37° C. The resulting RecA-DNA filaments were stored at 4° C. and used for imaging the same day.

Microscope Slide Preparation.

Quartz microscope slides (G. Finkenbeiner) were cleaned using Alconox detergent, followed by sonication for 15 minutes in acetone, 1 M aqueous KOH, ethanol, 1 M aqueous KOH, sequentially. Slides being prepared for lipid bilayers were submerged into a 5% HF solution for 2 hours after the second KOH step. Finally, the slides were rinsed with deionized water, and flame dried. The flow channels were prepared using two pieces of double-sided adhesive tape (3M) and covered with a No. 1.5 glass coverslip (VWR).

Oxygen Scavenging System.

All imaging buffers were supplemented with the oxygen scavenging system, which included 10% (w/v) glucose (Sigma), 0.1% (v/v) beta-mercaptoethanol (Sigma), 500 micrograms/mL glucose oxidase (Sigma), and 10 micrograms/mL catalase (Roche). The oxygen scavenging system was important for reliable photoswitching of the fluorophores. As low as 0.01% of beta-mercaptoethanol can be used in some instances for efficiently photoswitching of the cyanine dyes. The beta-mercaptoethanol can also be replaced by other reducing reagents such as glutathione and cysteins, in other embodiments.

Surface-Immobilization of DNA and Antibodies.

To immobilize the labeled dsDNA on a surface, quartz microscope slides (G. Finkenbeiner) were cleaned using Alconox detergent, sonicated in 1 M KOH, ethanol, and 1 M KOH sequentially before being rinsed with MilliQ water and flame dried. A biotinylated bovine serum albumin (BSA, Sigma) solution (1.0 mg/mL) was first added to the slides, followed by 0.25 mg/mL streptavidin (Invitrogen), and finally the DNA sample at a low concentration (~30 pM) in order to obtain a low surface density of DNA molecules such that individual molecules were well separated and optically resolvable. The slides were rinsed prior to the addition of each reagent.

To immobilize DNA constructs for the 3-color STORM imaging, three different DNA constructs, each labeled with an Alexa 405-Cy5 pair, a Cy2-Cy5 pair, or a Cy3-Cy5 pair were mixed in solution and co-immobilized onto a quartz slide as described above. A concentration of 500 pM of DNA was used to reach a high surface density of immobilized molecules.

To immobilize the DNA sample labeled with multiple switches on a quartz slide, a lipid bilayer was first formed on the slide by flowing in liposomes of egg PC and 5% biotin-PE (Avanti). The liposomes were formed according to the manufacturer's instructions, extruded through a 0.05 micrometer filter membrane at a concentration of 5 mg lipids/mL in DI water, and then mixed with a 1:1 ratio with a buffer containing 10 mM Tris at pH 8.0, 100 mM NaCl immediately before use. After a 2 hour incubation the bilayer was rinsed extensively with 50 mM Tris at pH 8.0, 10 mM NaCl, and the bilayer was incubated with streptavidin (0.25 mg/mL, Invitrogen) for 30 minutes. After extensive washing, the streptavidin surface was crosslinked in 4% v/v formaldehyde in PBS for 1 hour and rinsed with Tris buffer before allowing the biotinylated, switch-labeled DNA to bind. DNA was imaged in Tris buffer (50 mM Tris-Cl at pH 7.5, 10 mM NaCl) with the oxygen scavenging system described above.

To immobilized switch-labeled antibodies on a surface, the quartz slides were cleaned as described and incubated for 5 minutes with mouse anti-transferrin IgG (Abcam) allowing it to bind non-specifically. The slide was then incubated with the labeled secondary antibodies in PBS buffer containing 3% bovine serum albumin (BSA) for 10 min. The buffer was replaced with 50 mM Tris, 10 mM NaCl, pH 7.5 containing the oxygen scavenging system for imaging.

Immunofluorescence Imaging of RecA-dsDNA Filaments.

Biotinylated RecA-dsDNA filaments were attached via streptavidin linkages to a quartz slide non-specifically coated with biotinylated BSA. The surface was then washed with 50 mM Tris at pH 7.0, 100 mM NaCl, 7 mM $MgCl_2$, 3% BSA w/v (block buffer) and incubated for 30 minutes to block the surface against non-specific antibody binding. The slide was then incubated in this block buffer containing monoclonal mouse antibody against RecA (Stressgen) at 2 microgram/mL for 1 hour. After extensive washing with block buffer, the slide was incubated in the block buffer containing switch-labeled secondary antibody at 0.3 microgram/mL for 1 hour. Finally, the sample was washed and imaged in 50 mM Tris at pH 7.5, 100 mM NaCl, 7 mM $MgCl_2$, supplemented with the oxygen scavenging system as described above.

Immunofluorescence imaging of microtubules and clathrin-coated pits in cells. Green monkey kidney BS-C-1 cells were plated in LabTek II 8 well chambered coverglass (Nunc) at a density of 30 k per well. After 16 to 24 hr, they were rinsed with phosphate buffered saline (PBS) buffer, fixed with 3% formaldehyde, and 0.1% glutaraldehyde at room temperature in PBS for 10 minutes, and quenched with 0.1% sodium borohydride in PBS for 7 minutes to reduce the unreacted aldehyde groups and fluorescent products formed during fixation. The sodium borohydride solution was prepared immediately before use to avoid hydrolysis. The fixed sample was permeablized in blocking buffer (3% BSA, 0.5% Triton X-100 in PBS) for 10 min, stained with one or both of the primary antibodies against tubulin and clathrin (2.5 micrograms/mL mouse anti-beta (β) tubulin, ATN01 from Cytoskeleton and/or 2 micrograms/mL rabbit anti-clathrin heavy chain, ab21679 from Abcam) for 30 min in blocking buffer. The sample was then rinsed with washing buffer (0.2% BSA, 0.1% Triton X-100 in PBS) three times. Corresponding secondary antibodies labeled with photoswitchable probes (2.5 micrograms/mL) were added to the sample in blocking buffer and then thoroughly rinsed after 30 minutes. Cell imaging was performed in a standard imaging buffer that contained 50 mM Tris, pH 7.5, 10 mM NaCl, 0.5 mg/mL glucose oxidase (Sigma, G2133), 40 micrograms/mL catalase (Roche Applied Science, 106810), 10% (w/v) glucose and 1% (v/v) beta-mercaptoethanol. Beta-mercaptoethanol was found to be important for the observed photoswitching behavior of Cy5, Cy5.5, and Cy7, but even a low concentration of beta-mercaptoethanol (as low as 0.02% v/v, or potentially lower) supported photoswitching. Beta-mercaptoethanol at low concentrations (0.1%) was compatible with live cell imaging. Photoswitching was also observed when beta-mercaptoethanol was replaced with cysteine (100 mM), which was also compatible with live cell imaging. Glucose oxidase was used as an oxygen scavenger system to increase the photostability of the cyanine dyes, and cells were viable at the reported glucose oxidase concentration for at least 30 minutes.

Goat anti-mouse antibody (Invitrogen) and goat anti-rabbit antibody (Abcam) were each labeled with a mixture of amine-reactive activators and reporters. Alexa 405, Cy2, and Cy3 were used as the activating portion of the photoswitch. Alexa 647 (Invitrogen), which has very similar structural and optical properties as Cy5, was used as the light-emitting portion of the photoswitch. The concentrations of the reactive dyes were controlled such that each antibody had, on average, two activating dyes and 0.3-0.4 light-emitting dyes.

Imaging Procedures.

Photoswitch characterization, DNA concatamer imaging and RecA-dsDNA imaging were performed with an Olympus IX71 microscope. Single-molecule imaging was conducted in the prism-type total internal-reflection fluorescence (TIRF) imaging geometry. The samples were excited with a 657 nm laser, and activated with a 532 nm, a 457 nm or a 405 nm laser. The fluorescence emission of the dyes was collected with a N.A. 1.25 60× water immersion objective, and imaged onto an electron multiplying CCD camera (Andor Ixon DV897) after passing through a 665 nm long pass filter (Chroma). To track motion of the sample stage, 200 nm red fluorescent polystyrene beads (Invitrogen, F-8810) were added to the slide in Tris buffer containing 10 mM $MgCl_2$ and allowed to bind to the surface. Data was acquired using custom data acquisition software written in Labview, which enabled sequences of alternating red and green laser excitation pulses to be applied to the sample, switching the dyes on and off. Laser excitation was synchronized with the camera exposure to 1 ms accuracy.

Imaging experiments on DNA concatamers typically included of 60 laser pulse cycles to activate and deactivate the switches, where each cycle lasted for 5 s, so that the final image took 5 minutes to acquire. The multiple cluster configuration of the centroid position distribution is typically apparent within 2 minutes. The experiments on antibody-labeled RecA-dsDNA filaments included 70 switch cycles, each lasting 10 s. The ring shape of the RecA-dsDNA filaments typically became evident within 2 minutes, although the position of every switch present in the sample had not yet been identified by this time. As the rate of switching depended linearly on the excitation intensity, the cycling time, and hence the overall imaging time, could be shortened without substantially affecting the localization accuracy by increasing the red laser intensity. The green laser intensity was chosen so that typically 1-3 switches were switched on during the green pulse and, in most cases, all activated switched were turned off during the red phase of the cycle.

Raw images of RecA-dsDNA for comparison with STORM reconstructed images were formed by taking the maximum fluorescence value recorded for each pixel throughout the imaging sequence so that each switch would be equally represented regardless of the amount of time it spent in the fluorescent or dark states.

Three-color STORM imaging of the DNA sample was performed on an Olympus IX71 inverted microscope in the prism-type TIRF configuration. A 633 nm HeNe laser was used as the imaging laser and the violet (405 nm), blue (457 nm), and green (532 nm) lasers were used as the activation light sources. The sample was first exposed to the red imaging light to switch off nearly all Cy5 dyes in the field of view. Then the sample was periodically activated with a sequence of violet, blue, and green laser pulses each of which switched on a sparse, optically resolvable subset of fluorophores which were then imaged with the red laser. Fluorescence from these probes was detected with a CCD camera after passing through a long pass emission filter (Chroma, HQ645LP). During the STORM data acquisition, the camera recorded the fluorescence signal at a constant frame rate of 19 Hz. In each switching cycle, one of the activation lasers was turned on for 1 frame, followed by 9 frames of illumination with the red imaging laser.

STORM imaging of cells was performed on the Olympus IX71 microscope with an objective-type TIRF imaging configuration. A custom polychroic beamsplitter (z458/514/647rpc, Chroma) reflected the excitation laser light onto the sample through an objective (100× oil, NA 1.4, UPlanSApo, Olympus), and fluorescence emission from the sample was collected by the same objective. Emitted light was filtered with two stacked dual-band emission filters (51007m, Chroma, and 595-700DBEM, Omega Optical) before being imaged on the EMCCD camera. The use of a dual-band emitter enables fluorescence from Cy3 to be collected in addition to the fluorescence of the reporter dyes. Cy3 fluorescence collected during frames in which the green activation laser was on was used for drift correction purposes and to generate the conventional fluorescence image. For single-color STORM imaging with Alexa 647 as the light emitting portion of the photoswitch and Cy3 as the activating portion, the red laser (657 nm) was used for imaging and green (532 nm) laser pulses were for activation. For two-color STORM imaging with Cy2 and Cy3 as the activating portion, alternating blue and green (457 and 532 nm) laser pulses were used for activation. Images were acquired at a frame rate of 19 Hz. In each switching cycle, one of the activation lasers was turned on for 1 frame, followed by 9 frames of illumination with the red imaging laser. Typical laser powers used for STORM imaging were 40 mW for the red laser and 2 microwatts for each of the activation lasers.

Image Analysis.

In one example of image analysis, fluorescent structures in an averaged image were first isolated in 13×13 pixel square fitting window for data analysis. In a given window, the total fluorescence intensity was integrated in each frame to produce a fluorescence time trace (see FIG. 6). Several criteria were used to ensure high accuracy localization of single switches:

(1) In each switching cycle, only regions where a single switch is on for at least three frames (0.3 seconds) were used for localization analysis (see FIG. 6).

(2) The fluorescence images within these regions were fit by nonlinear least-squares regression to a continuous ellipsoidal Gaussian:

$$I(x,y) = A + I_0 e^{[-(x'/a)^2 - (y'/b)^2]/2}$$

where:

$$x' = (x-x_0)\cos\theta - (y-y_0)\sin\theta$$

$$y' = (x-x_0)\sin\theta + (y-y_0)\cos\theta$$

Here, A is the background fluorescence level, $I_0$ is the amplitude of the peak, a and b reflects the widths of the Gaussian distribution along the x and y directions, $x_0$ and $y_0$ describe the center coordinates of the peak, and $\theta$(theta) is the tilt angle of the ellipse relative to the pixel edges. Based on this fit, the peak ellipticity defined as $|2(a-b)/(a+b)|$ was computed. If this ellipticity exceeded 15%, indicating poor image quality or the possible presence of multiple active switches, the region was rejected from the analysis.

(3) The total number of counts collected in the peak was calculated as $2\pi$ ab $I_0$ (2 pi ab $I_0$) and then converted to photoelectrons, and thus the number of photons detected, using the camera manufacturer's calibrated curve for the electron multiplication and ADC gain settings used during imaging. If the total number of photoelectrons in the peak was less than 2,000, the region was rejected due to insufficient statistics to achieve high localization accuracy.

The regions of the fluorescence traces that passed the above tests were used for the final localization analysis. The fluorescence images corresponding to these regions were subjected to a final fit using a pixelated Gaussian function to determine the centroid position. Because the CCD chip included square pixels of finite size, for optimum accuracy, the image was fit to:

$$I(x,y) = A + \int_{x-\delta}^{x+\delta} dX \int_{y-\delta}^{y+\delta} dY \, I_0 e^{[-(\frac{X-x_0}{a})^2 - (\frac{Y-y_0}{b})^2]/2}$$

which, for ease of evaluation, can be re-expressed in terms of error functions as:

$$I(x,y) = A + I_0 \frac{ab\pi}{4}\left[\text{erf}\left(\frac{x+\delta-x_0}{a}\right) - \text{erf}\left(\frac{x-\delta-x_0}{a}\right)\right]\left[\text{erf}\left(\frac{y+\delta-y_0}{b}\right) - \text{erf}\left(\frac{y-\delta-y_0}{b}\right)\right]$$

where A, $I_0$, a, b, $x_0$ and $y_0$ are as defined previously and $\delta$(delta) is the fixed half-width of a pixel in the object plane. The final centroid coordinates ($x_0$, $y_0$) obtained from this fit were used as one data point in the final STORM image.

In another example of image analysis, an image movie was prepared that included a repetitive sequence of activation frames (in which the activation laser is on) and imaging frames (in which the imaging laser is on). For each imaging frame, fluorescent spots were identified and fit to Gaussian and/or elliptical Gaussian functions to determine their centroid positions, intensities, widths, and ellipticities. Based on these parameters, peaks too dim, too wide or too skewed to yield satisfactory localization accuracy were rejected from further analysis. Peaks appearing in consecutive imaging frames with a displacement smaller than one camera pixel were considered to originate from the same fluorescent molecule and centroid positions of these peaks were connected across frames and organized into a data structure, which is referred to as a "string." Each string represents a single switching cycle for one fluorescent reporter molecule: the starting point of the string is the frame in which the molecule is switched on and its endpoint is the frame in which the molecule switches off. The final localization of the molecule was determined as the weighted average of the centroid positions across the entire string, weighted by the peak intensity of each frame. The total number of photons detected for each switching cycle was used as an additional filter to further reject localizations with low accuracy. Strings starting in an imaging frame immediately after an activation frame were recognized as a controlled activation event and color-coded according to the activation laser color. Other strings were identified as non-specific activations, most likely induced by the red imaging laser.

To correct for mechanical drift in the microscope during imaging, the same fitting algorithm was used to automatically track the motion of several fluorescent beads in the field of view. The beads served as fiducial marks and their positions were sampled during each imaging cycle. The averaged motion of the beads was subtracted from the coordinates obtained for each single switch position, yielding a drift-corrected reconstructed image.

As another drift correction method, the activator fluorophores was imaged during the activation frame and the correlation function was calculated between the first activation frame and all subsequent activation frames. By tracking the centroid of the correlation function, the drift of the image could be determined and corrected for in the STORM image. The correlation functions obtained from the fiducial marker images may also be used for drift correction. In some cases, it was also found that some further drift correction was possible by analyzing the correlation function of the STORM image itself as a function of time.

For quantitative analysis of images using switches equally spaced on dsDNA, the coordinates in the reconstructed image were classified using a k-means clustering algorithm, and inter-switch distances were calculated as the distance between the cluster centroids. The number of clusters input to the algorithm was chosen according to the number of photobleaching steps observed during the initial exposure to red light.

Prediction of DNA Configuration.

Possible configurations of a 135 bp piece of dsDNA bound to the surface were computed by Monte Carlo simulation of the DNA as a worm-like chain in the plane. According to the Watson-Crick structure of dsDNA and accounting the length of the $C_6$ linkers attaching the Cy5 molecules to the nucleotides, the expected contour length between neighboring Cy5 molecules of 46±1 nm was calculated. The DNA was treated as a series of 1 Å (Angstrom) joints lying in the plane, each of which was deflected by a random angle selected from a Gaussian distribution chosen to give a persistence length of 50 nm. The measured inter-switch spacing was compared to the distribution of end-to-end distances of the polymer in this simulation.

Single-Molecule Imaging of Photoswitchable Activator-Reporter Pairs.

To characterize the switching kinetics of the photoswitchable probes from above, the two fluorescent dye molecules (activator and reporter) were conjugated to the end of a double stranded DNA (dsDNA) construct, and the construct was immobilized on a quartz surface for single-molecule imaging. The DNA constructs were labeled as follows. Briefly, PAGE purified DNA oligonucleotides with biotin and/or amine modification at the ends were obtained from Operon. The oligos (30 base pairs (bp) in length) were labeled with amine reactive dyes (Cy2, Cy3, Cy5, Cy5.5, and Cy7 were obtained from GE Healthcare, and Alexa Fluor 405 and Alexa Fluor 647 were obtained from Invitrogen) post-synthetically following the protocol provided by the manufacturers. The dye-labeled oligos were purified using reverse phase HPLC. Complementary strands of DNA, each labeled with an activator or a reporter dye, were annealed to form biotinylated dsDNA by mixing equimolar amounts of the two complementary strands in 10 mM Tris-Cl (pH 7.5), 50 mM NaCl. This allowed a pair of activator and reporter dyes to be brought into close proximity, as illustrated in FIG. 13H, facilitating the immobilization of dye pair to a microscope slide via biotin-streptavidin linkage FIG. 13H is a schematic of double-stranded DNA and antibody molecules labeled with a Cy3-Cy5 pair.

To immobilize the labeled dsDNA on a surface, quartz microscope slides (G. Finkenbeiner) were cleaned using Alconox detergent, sonicated in 1M KOH, ethanol, and 1M KOH sequentially before being rinsed with MilliQ water and flame dried. A biotinylated bovine serum albumin (b-BSA, Sigma) solution (1.0 mg/mL) was first added to the slides, followed by 0.25 mg/mL streptavidin (Invitrogen), and finally the DNA sample at a low concentration (~30 pM) in order to obtain a low surface density of DNA molecules such that individual molecules were well separated and optically resolvable from each other. The slides were rinsed prior to the addition of each reagent. Single-molecule imaging was performed in a standard imaging buffer that contains 50 mM Tris, pH 7.5, 10 mM NaCl, 0.5 mg/mL glucose oxidase (Sigma, G2133), 40 micrograms/mL catalase (Roche Applied Science, 106810), 10% (w/v) glucose and 1% (v/v) beta-mercaptoethanol.

Single-molecule imaging was performed on an Olympus IX-71 inverted microscope equipped with prism-type total internal reflection fluorescence (TIRF) configuration. A red 657 nm diode laser (RCL-200-656, Crystalaser) was used to excite fluorescence from the reporter fluorophore and to switch them off to the dark state. A 532 nm diode-pumped solid state laser (GCL-200-L, Crystalaser), the 457 nm line of an Ar ion laser (35-LAL-030-208, Melles Griot), and a 405 nm diode laser (CUBE 405, Coherent) were used to reactivate the reporters by exciting the different activators. The fluorescence signal from the reporter dyes was collected by a 60×, NA 1.2 water immersion objective (Olympus) and then imaged on to an EMCCD camera (Andor Ixon DV897DCS-BV) after passing through a band pass fluorescence emission filter (Chroma, HQ710/80m for Cy5 and Cy5.5 and HQ740LP for Cy7). A 1.6× tube lens was used to set the final imaging magnification to ~100×.

Switching Kinetics Analysis of the Photoswitchable Dyes.

To measure switching kinetics, the DNA samples were first illuminated with the red imaging laser (657 nm) to switch the reporter molecules into the dark state, and the rate at which they switched off ($k_{off}$) was measured by recording the number of fluorescent molecules as a function of time and fitting it to a single exponential function. For measurements of $k_{on}$, after switching the reporter fluorophores off and while the red imaging laser remained on, the sample was exposed to the activation laser (405 nm, 457 nm, or 532 nm), which caused the fluorophores to switch back on, reaching equilibrium between activation and deactivation. The number of fluorophores in the fluorescent state at equilibrium was measured, and the activation rate constant ($k_{on}$) was then calculated from the independently determined value of $k_{off}$ and the fraction of molecules (F) in the fluorescent state at equilibrium, according to the relation $F=k_{on}/(k_{on}+k_{off})$.

Photon Number Analysis of the Photoswitchable Dyes.

The number of photons detected per switching cycle for Cy5, Cy5.5, and Cy7 were measured when they were paired with Cy3 as the activator on DNA and antibody molecules. The average number of photons detected per switching cycle was a constant independent of the excitation laser intensity. The photon number, however, depended on the emission filters and imaging geometry used. Using the prism-type TIRF imaging geometry, 657 nm imaging laser, and two stacked HQ665LP emission filters for Cy5 and Cy5.5 and a HQ740LP emission filter for Cy7, the photon numbers detected were ~3000 for Cy5 and Cy5.5 and ~500 for Cy7. These numbers correspond to a theoretical limit of localization accuracy (in terms of standard deviation or s.d.) of 3 nm for Cy5 and Cy5.5 and 9 nm for Cy7, calculated using the formula $s.d.=\sqrt{(S^2+a^2/12)/N+4\sqrt{\pi}S^3b^2/aN^2}$. In the formula, S is the standard deviation of the point spread function of the imaging setup, a is the edge size of the area imaged on each CCD pixel, b is the background noise level, and N is the number of photons detected (S=173 nm for Cy5/Cy5.5 and =200 nm for Cy7, a=165 nm, b=6 for Cy5/Cy5.5 and =1 for Cy7).

In this work, full-width-half-maximum (FWHM) was typically used to describe imaging resolution. The FWHM values corresponding to the localization accuracies quoted above are 8 nm for Cy5 and Cy5.5 and 22 nm for Cy7. Using the objective-type TIRF imaging geometry, 657 nm imaging laser, and stacked HQ665LP and HQ710/70BP emission filters for Cy5 and Cy5.5 and stacked HQ740LP and 800WB80 emission filters for Cy7, the photon numbers detected were ~6000 for Cy5 and Cy5.5 and ~1000 for Cy7, which were approximately twice as high as the numbers obtained in the prism-type TIRF geometry. The number of photons detected for Alexa 647, a cyanine dye with a similar structure to that of Cy5 (see FIG. 13A), was within 10% of the number detected from Cy5. FIGS. 13A-13D illustrate structures of the photoswitchable reporters Cy5, Alexa 647, Cy5.5, and Cy7. "R" stands for the place where DNA or antibody was attached. The photon numbers detected from the activator-reporter-labeled DNA samples were slightly smaller than the numbers detected from the corresponding antibody samples. The HQ665LP, HQ740LP, and HQ710/70BP filters were obtained from Chroma and the 800WB80 filter was from Omega.

Figure 14:
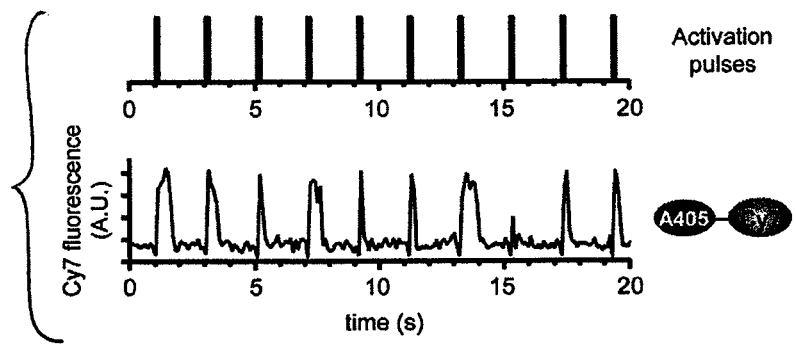
FIG. 14 illustrates photoswitching behavior of Alexa 405-Cy7, in one embodiment of the invention.

FIGS. 13E-13F illustrate normalized absorption and emission spectra of Cy5, Alexa 647, Cy5.5, and Cy7 in aqueous solution. The absorption spectra were normalized by the maximum absorption value, and the emission spectra were normalized by the integrated peak area. FIG. 13G illustrates normalized absorption spectra of activator dyes, Alexa 405, Cy2, and Cy3 in aqueous solution. FIG. 14 illustrates photoswitching behavior of the Alexa 405-Cy7 pair. The lower panel shows a fluorescence time trace of Cy7. The upper panel shows the 405 nm laser pulses used to activate the dye pair. A red laser (657 nm) was continuously on, serving to excite fluorescence from the Cy7 and to switch it off to the dark state.

Figure 15:
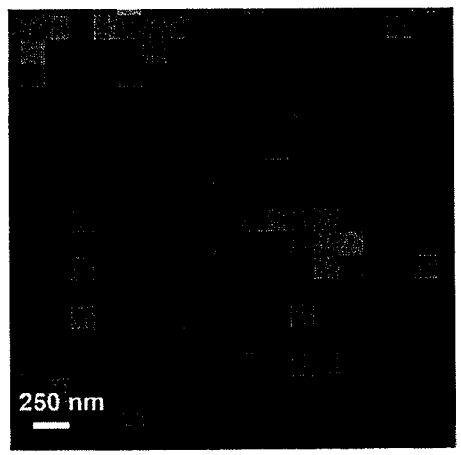
FIG. 15 is a conventional fluorescence image of certain DNA constructs labeled with Cy3-Cy5, Cy2-Cy5, or Alexa 405-Cy5, in an embodiment of the invention.

FIG. 15 shows a conventional fluorescence image of a mixture of three different DNA constructs, each labeled with Cy3-Cy5, Cy2-Cy5, or Alexa 405-Cy5 and mixed at a high surface density on a microscope slide. The fluorescence image was taken from all of the Cy5 molecules in this region before the sample was subjected to any photoswitching. A thermal color scheme is used here to illustrate the intensity, with black indicating low intensity, red higher, and yellow highest. A three-color image of the same region is shown in FIG. 12A. The overall intensity profile may appear to be slightly different for the two images due to the different numbers of switching cycles exhibited by individual molecules.

Three-Color Imaging of a Model DNA Sample.

Three different DNA constructs, each labeled with an Alexa 405-Cy5 pair, a Cy2-Cy5 pair, or a Cy3-Cy5 pair were mixed in solution and co-immobilized onto a quartz slide as described above. A concentration of 500 pM of each DNA was used to reach a high surface density of immobilized molecules. Due to a moderate Cy5 quenching effect that occurred when a Cy3 molecule was positioned in very close proximity, in this experiment these two dyes were separated by 9 base pairs on a 43 bp dsDNA, instead of being attached to the end of a dsDNA. This Cy5 quenching effect was less significant when Alexa 405 or Cy2 was positioned in very close proximity. Fluorescent beads (Molecular probes, F8801) were added to the sample slide as fiducial markers for the purpose of drift correction.

Imaging was performed on an Olympus IX71 inverted microscope in the prism-type TIRF configuration. A 633 nm HeNe laser (25-LHP-928-249, Melles Griot) was used as the imaging laser and the violet (405 nm), blue (457 nm), and green (532 nm) lasers mentioned above were used as the activation light sources. The sample was first exposed to the red imaging light to switch off nearly all Cy5 dyes in the field of view. Then the sample was periodically activated with a sequence of violet, blue, and green laser pulses each of which switched on a sparse, optically resolvable subset of fluorophores which were then imaged with the red laser. Fluorescence from these probes was detected with the CCD camera after passing through a long pass emission filter (Chroma, HQ645LP). During data acquisition, the camera recorded the fluorescence signal at a constant frame rate of 19 Hz. In each switching cycle, one of the activation lasers was turned on for 1 frame, followed by 9 frames of illumination with the red imaging laser. Under typical imaging conditions, an average fluorophore remains in the fluorescent state for three frames after activation, and ~3000 photons per molecule were detected during each switching cycle.

Imaging of Microtubules and Clathrin-Coated Pits in Cells.

Green monkey kidney BS-C-1 cells were plated in LabTek II 8 well chambered coverglass (Nunc) at a density of 30K per well. After 16 to 24 hr, cells were rinsed with phosphate buffered saline (PBS) buffer, fixed with 3% formaldehyde, and 0.1% glutaraldehyde at room temperature in PBS for 10 min, and quenched with 0.1% sodium borohydride in PBS for 7 min to reduce the unreacted aldehyde groups and fluorescent products formed during fixation. The sodium borohydride solution was prepared immediately before use to avoid hydrolysis. The fixed sample was permeablized in blocking buffer (3% BSA, 0.5% Triton X-100 in PBS) for 10 min, stained with one or both of the primary antibodies against tubulin and clathrin (2.5 micrograms/mL mouse anti-beta tubulin, ATN01 from Cytoskeleton and 2 micrograms/mL rabbit anti-clathrin heavy chain, ab21679 from Abcam) for 30 min in blocking buffer. The sample was then rinsed with washing buffer (0.2% BSA, 0.1% Triton X-100 in PBS) three times. Corresponding secondary antibodies labeled with photoswitchable probes (2.5 micrograms/mL) were added to the sample in blocking buffer and then thoroughly rinsed after 30 min. Cell imaging was performed in a standard imaging buffer that contains 50 mM Tris, pH 7.5, 10 mM NaCl, 0.5 mg/mL glucose oxidase, 40 micrograms/mL catalase, 10% (w/v) glucose and 1% (v/v) beta-mercaptoethanol. It was found that beta-mercaptoethanol was important for the observed photoswitching behavior of Cy5, Cy5.5, and Cy7, but even low concentrations of beta-mercaptoethanol (as low as 0.02% v/v) supported photoswitching. Beta-mercaptoethanol at low concentrations (0.1% and 0.02%) was compatible with live cell imaging. Photoswitching was also observed when beta-mercaptoethanol was replaced with cysteine (100 mM), which was also compatible with live cell imaging. Glucose oxidase was used as an oxygen scavenger system to increase the photostability of the cyanine dyes, and cell morphology was normal at the reported glucose oxidase concentration for at least 30 min. In this work, all imaging experiments were performed on fixed cells.

Goat anti-mouse antibody (Invitrogen) and goat anti-rabbit antibody (Abcam) were each labeled with a mixture of amine-reactive activators and reporters. Cy2 and Cy3 were used as the activators. Alexa 647 (Invitrogen), which has similar structural and optical properties to Cy5 (FIG. 13), was used as the reporter. The concentrations of the reactive dyes were controlled such that each antibody had, on average, two activator molecules and 0.3 to 0.4 reporter molecules. The photoswitching behavior was relatively insensitive to the number of activators per antibody. The labeling ratio of two activators per antibody was chosen to ensure that the majority of antibodies had activators and thus to optimize the staining efficiency. However, when more than one reporter molecule was attached to the same antibody, it was found that the close proximity of the reporter molecules lowered the off rate. To assess this effect more quantitatively, dsDNA molecules labeled with two Cy5 dyes of known separations were prepared. The off rate of the construct having two Cy5 dyes separated by 2 nm was ~5 times slower than that for a construct with a single Cy5. For constructs where the two Cy5 dyes were separated by 7 nm or 14 nm, the off rates were roughly comparable to that of the single-Cy5 construct. This self-interaction effect was slightly less pronounced for Alexa 647 as compared with Cy5. Practically, when labeling antibody, a relatively low dye/protein ratio was chosen here for the reporter (0.3 to 0.4) such that the majority of reporter-labeled antibody molecules have only one reporter.

Imaging was performed on the Olympus IX71 microscope with an objective-type TIRF configuration. A custom polychroic beamsplitter (z458/514/647rpc, Chroma) reflected the excitation laser light onto the sample through an objective (100× oil, NA 1.4, UPlanSApo, Olympus), and fluorescence emission from the sample was collected by the same objective. Emitted light was filtered with two stacked dual-band emission filters (51007m, Chroma, and 595-700DBEM, Omega optical) before being imaged on the EMCCD camera. The use of a dual-band emitter enables fluorescence from Cy3 to be collected in addition to the fluorescence of the reporter dyes. Cy3 fluorescence collected during frames in which the green activation laser was on was used for drift correction purposes and to generate the conventional fluorescence image. For single-color imaging with Alexa 647 as the reporter and Cy3 as the activator, the red laser (657 nm) was used for imaging and green (532 nm) laser pulses were for activation. For two-color imaging with Cy2 and Cy3 as the activators, alternating blue and green (457 and 532 nm) laser pulses were used for activation. Images were acquired at a frame rate of 19 Hz. In each switching cycle, one of the activation lasers was turned on for 1 frame, followed by 9 frames of illumination with the red imaging laser. Because the two stacked dual-band emission filters (51007m and 595-700DBEM) significantly cut fluorescence signal from Alexa 647, only ~3000 photons, instead of ~6000, were detected on average from one antibody during each switching cycle. Typical laser powers used for imaging were 40 mW for the red laser and 2 microwatts for each of the activation lasers.

Image Analysis.

A typical image was generated from a sequence of 2000 to 100000 image frames recorded at 19 Hz. The movie included a repetitive sequence of activation frames (in which the activation laser is on) and imaging frames (in which the imaging laser is on). For each imaging frame, fluorescent spots were identified and fit to a Gaussian or elliptical Gaussian function to determine their centroid positions, intensities, widths and ellipticities. Based on these parameters, peaks too dim, too wide or too elliptical to yield satisfactory localization accuracy were rejected from further analysis. Peaks appearing in consecutive imaging frames with a displacement smaller than one camera pixel were considered to originate from the same fluorescent molecule, and centroid positions of these peaks were connected across frames and organized into a data structure which is referred to here as a "string." Each string represents a single switching cycle for one fluorescent reporter molecule: the starting point of the string is the frame in which the molecule is switched on and its endpoint is the frame in which the molecule switches off. The final localization of the molecule was determined as the weighted average of the centroid positions across the entire string, weighted by the number of photons detected in each frame. The total number of photons detected for each switching cycle was used as an additional filter to further reject localizations with low accuracy. Strings starting in an imaging frame immediately after an activation frame were recognized as a controlled activation event and color-coded according to the activation laser color. Other strings were identified as non-specific activations, most likely induced by the red imaging laser as the amount of non-specific activation was observed to increase with the red laser intensity (data not shown). Nonspecific activation by the red imaging laser would also occur in the first imaging frame and be counted as a controlled activation event, giving one source of error for color crosstalk.

Besides the number of photons detected in one imaging cycle, another factor that limits the localization accuracy was sample drift during the course of the experiment. The drift was corrected by two methods. The first method involved adding fiducial markers (fluorescent beads) to track the drift of the sample and subtracting the movement of the markers during image analysis. In the second method, the activator fluorophores were imaged during the activation frame and calculated the correlation function between the first activation frame and all subsequent activation frames. By tracking the centroid position of the correlation function, the drift of the image can be determined and corrected for in the image. The correlation functions obtained from the fiducial marker images may also be used for drift correction. In some cases, it was found that further drift correction was possible by analyzing the correlation function of the image itself as a function of time.

For image presentation, each localization was assigned as one point in the image. These points were either represented by a small marker (e.g. a cross) or rendered as a normalized 2D Gaussian peak, the width of which was determined by its theoretical localization accuracy calculated from the number of photons detected for that localization event. For multi-color images, each localization was also false-colored according to the color of the activation laser pulse. The following color coding scheme was typically used (although other coding schemes are possible): activations by the violet (405 nm) laser were shown in blue, those by the blue (457 nm) laser were shown in green, and those by the green (532 nm) laser were shown in red.

Crosstalk between different color channels resulted mainly from two effects: nonspecific activation and false activation. As described earlier, nonspecific activations, mostly likely induced by the red imaging laser, can be most easily identified if the string did not start immediately after an activation frame. However, such a nonspecific activation may also occur during the frame immediately after an activation laser pulse and thus be incorrectly assigned a color, although this mis-assignment will occur with a relatively low probability. Three methods can be used to reduce nonspecific activation-induced crosstalk: (1) increasing the activation laser intensity, providing that the density of activated probes remains low enough for single-molecule localization; (2) using a faster frame rate which effectively improves identification of those molecules activated by the activation laser pulse; and (3) decreasing the imaging laser intensity to reduce the non-specific activation rate, but at the cost of reducing imaging speed and/or accuracy. The second source of color crosstalk, false activations, stems from probes which were switched on by the wrong activation laser. Combining these two sources, the overall crosstalk ratios under the typical cell imaging conditions used here were measured to be 15% to 25% for the leakage of Cy2 signal into the Cy3 channel and 25 to 35% for the leakage of Cy3 signal into the Cy2 channel. For the three-color imaging of the DNA sample, crosstalk effects were observed to be somewhat smaller because nonspecific activation was observed to be less pronounced (FIG. 16), in part due to stronger activation laser powers used.

Figure 16:
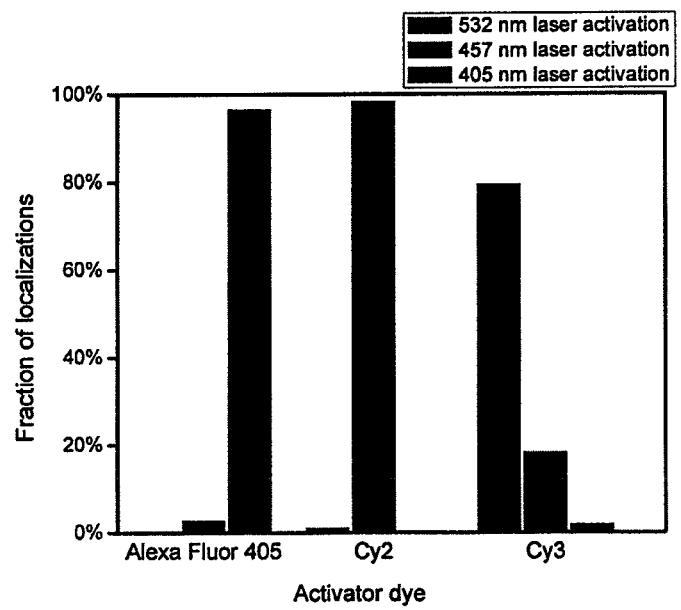
FIG. 16 shows crosstalk analysis for a three-color image of a DNA sample, in another embodiment of the invention.

FIG. 16 shows crosstalk analysis for the three-color image of the DNA sample. The image shows separated clusters of localizations, each cluster corresponding to an individual DNA molecule (FIGS. 12A-12C). Each of the localizations was colored according the activation laser used: localizations activated by the 405 nm laser were assigned the blue color, those activated by the 457 nm laser were assigned the green color and those activated by the 532 nm laser were assigned the red color. The majority of the localizations within each cluster displayed the same color, identifying the type of activator dye (Alexa 405, Cy2, or Cy3) present on the DNA molecule. The numbers of localizations of each color were counted for individual clusters and the fractions of localizations assigned to each color channel are plotted here for the Alexa 405, Cy2; and Cy3 clusters. The crosstalk ratios can be calculated from the ratios of incorrectly to correctly colored localizations.

The crosstalk ratios between different color channels under each imaging condition can be quantitatively determined using samples singly labeled with only one of the photoswitchable probes. Due to the clear separation between clathrin-coated pits and microtubules, the two color cell image itself can also be used to estimate crosstalk quantitatively. Using the crosstalk ratios, crosstalk can be effectively subtracted from a multicolor image. For instance, in the case of a two-color image, at any given location:

$$\begin{cases} D_1 = d_1 + C_{2 \to 1} d_2 \\ D_2 = C_{1 \to 2} d_1 + d_2 \end{cases}$$

where $D_1$ and $D_2$ are the observed local densities of spots in color channels 1 and 2, respectively, and $d_1$ and $d_2$ are the corresponding true local densities. $C_{1 \to 2}$ and $C_{2 \to 1}$ are the crosstalk ratios between the two channels. The values of $d_1$ and $d_2$ can be solved from observed local densities $D_1$ and $D_2$ and crosstalk ratios $C_{1 \to 2}$ and $C_{2 \to 1}$. Thus the probability of a localization at a given position in channel 1 being assigned the wrong color is simply $P_1 = 1 - d_1/D_1$. This point can thus be removed according to this probability. Similar treatment can be applied to every points in channels 1 and 2. To correct color crosstalk in the two-color images, a radius of 35 nm was chosen to calculate the local densities. Due to the finite area required to reliably calculate local densities, a slight erosion effect will arise from the crosstalk subtraction where two different colored structures overlap in space. According to simulations, for this example, if the imaging resolution is 20 to 30 nm, such an operation will reduce the spatial resolution by ~20% when the crosstalk ratio is 20% for both channels. A similar statistical approach can also be used to assign colors to nonspecific activations (e.g. the probability of a non-specific activation belong to color channel 1 is $d_1/(d_1+d_2)$, where $d_1$ and $d_2$ were obtained from controlled activations as described above), effectively increasing the overall localization point densities in the images, which may help improve resolution in cases where the resolution is point-density limited. Crosstalk subtraction and nonspecific activation color assignment were applied in FIG. 11.

Figure 17:
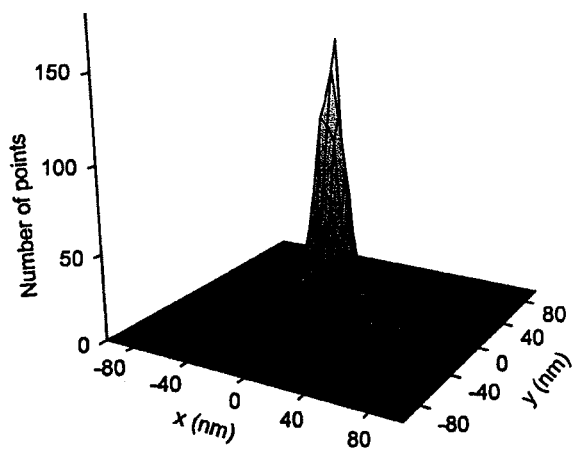
FIG. 17 shows localization accuracy for a single-color image of a cell, in one embodiment of the invention.

FIG. 17 shows localization accuracy for a single-color image of the cell. The localization accuracy was determined from point-like objects in the cell, appeared as small clusters of localizations away from any discernable microtubule filaments. Shown here is the spatial distribution of localizations within these point-like clusters. The 2D histogram of localizations was generated by aligning 170 clusters by their center of mass, each cluster containing more than 8 localizations. Fitting the 2D histogram with a Gaussian function gives a FWHM of 24 nm.

Figure 18:
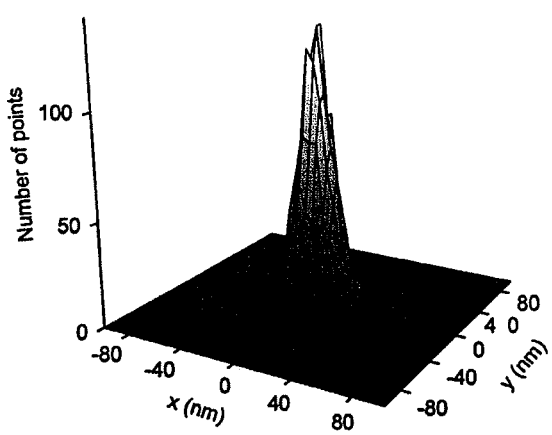
FIG. 18 shows localization accuracy for a two-color image of a cell, in another embodiment of the invention.
Figure 20D:
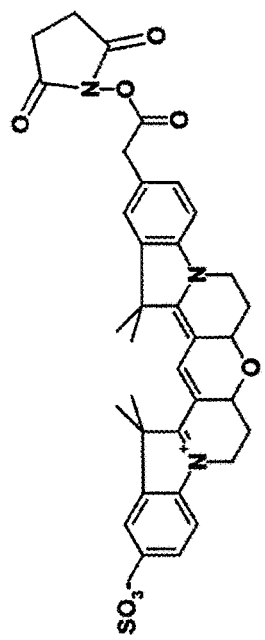
Figure 20E:
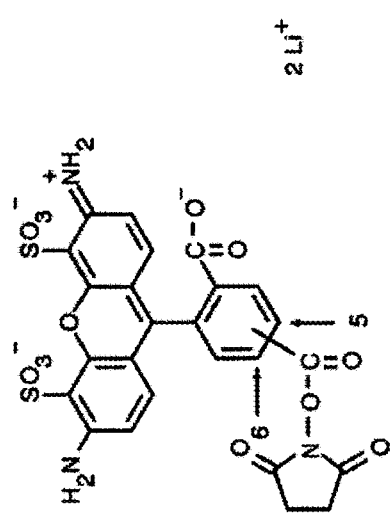
Figure 20F:
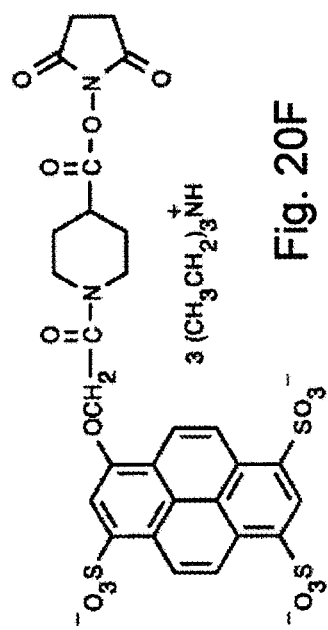

FIG. 18 shows localization accuracy for a two-color image of the cell. The localization accuracy was also determined from point-like objects in the cell, appeared as small clusters of localizations away from any discernable microtubule or CCP structures. Shown here is the spatial distribution of localizations within these point-like clusters. The 2D histograms of localizations were generated by aligning 187 clusters by their center of mass, each cluster containing more than 8 localizations. Fitting the 2D histogram with a Gaussian function gives a FWHM of 30 nm.

FIG. 19 shows images of clathrin-coated pits (CCPs). FIG. 19A shows a comparison of conventional fluorescence images (upper panels) and the images generated here (lower panels). Nearly all CCPs appear to adopt a spherical structure. The rightmost panel shows two close-by CCPs that were resolved here, but appeared as a single nearly diffraction-limited spot in the conventional fluorescence image. FIG. 19B shows the size distribution of 300 CCPs determined from the images as shown in FIG. 19A.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system, comprising:
a first light source which applies activation light for activating a part of a plurality of photoswitchable entities into a state able to emit light;
a second light source which applies excitation light for exciting at least a part of the activated entities;
a detector which detects at least a part of light emitted from the excited entities; and
a controller, wherein the controller is programmed to: calculate positional information of at least a part of the plurality of entities by using information contained in the detected light, correct the positional information by using a fiduciary marker and movements of the fiduciary marker.

2. The system of claim 1, wherein the entities are fluorescent proteins.

3. The system of claim 1, wherein the entities are cyanine dyes.

4. The system of claim 3, wherein the cyanine dyes comprise at least one of Cy5, Cy5.5, Cy7, Alexa Fluor® 647, Alexa Fluor® 405, Alexa Fluor® 488, Cy2, Cy3, Cy3.5, Cy5, and a conjugate thereof.

5. The system of claim 1, wherein the fiduciary marker is a fluorescent particle.

6. The system of claim 1, wherein the controller is able to use Gaussian fitting to calculate the positional information.

7. The system of claim 1, wherein the controller is able to use elliptical Gaussian fitting to calculate the positional information.

8. The system of claim 1, wherein the activation light and the excitation light have substantially the same wavelength.

9. The system of claim 1, wherein the activation light and the excitation light have different wavelengths.

10. The system of claim 1, wherein the controller is able to generate an image by using the calculated positional information.

11. The system of claim 10, wherein the image is a high resolution image.

12. The system of claim 1, wherein the plurality of entities comprises a first entity and a second entity.

13. The system of claim 12, wherein:
the first entity is activatable by a first wavelength of activation light and
the second entity is activatable by a second wavelength of activation light.

14. The system of claim 12, wherein:
the first entity is excitable by a first wavelength of excitation light and
the second entity is excitable by a second wavelength of excitation light.

15. The system of claim 1, wherein the entities have a first portion and a second portion, the first portion being a light emitting portion and the second portion being an activator portion.

16. The system of claim 1, wherein the controller is able to calculate positional information of at least some of the plurality of entities to a resolution smaller than 20 nm.

17. The system of claim 1, wherein the controller is able to use the positional information to construct an image, the image having a resolution that is better than the diffraction-limited resolution of the emitted light.

18. The system of claim 1, wherein the controller is able to calculate the positional information of the at least a part of the plurality of entities at more than one point of time and/or as a function of time.

19. The system of claim 1, wherein at least some of the plurality of entities are activatable by light of different wavelengths and/or emit light at different wavelengths.

20. The system of claim 1, wherein the correction of the positional information comprises drift correction.

21. A program for causing a machine to perform a procedure of calculating positional information performed by a system as claimed in claim 1.

22. A storage medium comprising a program for causing a machine to perform a procedure of calculating positional information performed by a system as claimed in claim 1.

23. An article, comprising a storage medium comprising a program for causing a machine to perform a procedure of calculating positional information performed by a system as claimed in claim 1.

24. A method, comprising:

applying activation light for activating a part of a plurality of photoswitchable entities into a state able to emit light;

applying excitation light for exciting at least a part of the activated entities;

detecting at least a part of light emitted from the excited entities; and calculating positional information of at least a part of the plurality of entities by using information contained in the detected light, correcting the positional information by using a fiduciary marker and movements of the fiduciary marker.

25. The method of claim 24, wherein the correction is drift correction.

* * * * *

UNITED STATES PATENT AND TRADEMARK OFFICE
CERTIFICATE OF CORRECTION

PATENT NO. : 10,073,035 B2
APPLICATION NO. : 15/252307
DATED : September 11, 2018
INVENTOR(S) : Xiaowei Zhuang et al.

Page 1 of 1

It is certified that error appears in the above-identified patent and that said Letters Patent is hereby corrected as shown below:

On the Title Page

Item [63]:
Related U.S. Application Data: please correct the priority information to read:
This application is a continuation of 14/101,071, filed on Dec. 9, 2013, which is a continuation of application No. 12/795,423, filed on Jun. 7, 2010, which is a continuation of application No. 12/012,524, filed on Feb. 1, 2008, now Pat. No. 7,838,302, which is a continuation-in-part of application No. PCT/US2007/0176618, filed on Aug. 7, 2007, which is a continuation-in-part of application No. 11/605,842, filed on Nov. 29, 2006, now Pat. No. 7,776,613, said application No. 12/012,524 is a continuation-in-part of application No. 11/605,842, filed on Nov. 29, 2006, now Pat. No. 7,776,613.

Signed and Sealed this
Twenty-third Day of July, 2019

Andrei Iancu
*Director of the United States Patent and Trademark Office*